(12) United States Patent
Saito et al.

(10) Patent No.: US 11,304,919 B2
(45) Date of Patent: Apr. 19, 2022

(54) UTILIZATION OF CILASTATIN IN INHIBITING RENAL DISORDER

(71) Applicants: NIIGATA UNIVERSITY, Niigata (JP); Denka Company Limited, Tokyo (JP)

(72) Inventors: Akihiko Saito, Niigata (JP); Sawako Goto, Niigata (JP); Yoshiaki Hirayama, Tokyo (JP); Sakari Sekine, Tokyo (JP)

(73) Assignees: Niigata University; Denka Company Limited

( * ) Notice: Subject to any disclaimer, the term of this patent is extended or adjusted under 35 U.S.C. 154(b) by 0 days.

(21) Appl. No.: 17/050,883

(22) PCT Filed: Apr. 26, 2019

(86) PCT No.: PCT/JP2019/017963
§ 371 (c)(1),
(2) Date: Oct. 27, 2020

(87) PCT Pub. No.: WO2019/208777
PCT Pub. Date: Oct. 31, 2019

(65) Prior Publication Data
US 2021/0228522 A1 Jul. 29, 2021

(30) Foreign Application Priority Data

Apr. 27, 2018 (JP) .............................. JP2018-087294
Nov. 30, 2018 (JP) .............................. JP2018-225035

(51) Int. Cl.
*A61K 31/198* (2006.01)
*A61P 13/12* (2006.01)
*A61K 9/00* (2006.01)
*A61K 49/04* (2006.01)

(52) U.S. Cl.
CPC .......... *A61K 31/198* (2013.01); *A61K 9/0019* (2013.01); *A61K 49/04* (2013.01); *A61P 13/12* (2018.01)

(58) Field of Classification Search
None
See application file for complete search history.

(56) References Cited

U.S. PATENT DOCUMENTS

| | | | |
|---|---|---|---|
| 2008/0051428 | A1 | 2/2008 | Davis et al. |
| 2011/0165264 | A1 | 7/2011 | Jorge et al. |
| 2016/0324813 | A1 | 11/2016 | Saito et al. |

FOREIGN PATENT DOCUMENTS

| | | |
|---|---|---|
| JP | 2003-261459 | 9/2003 |
| JP | 2009-535410 | 10/2009 |
| JP | 2010-090094 | 4/2010 |
| KR | 10-2017-80086851 | 7/2017 |
| KR | 2017-0086851 | 7/2017 |
| WO | WO 2015/111666 | 7/2015 |

OTHER PUBLICATIONS

Lau et al (J Clin Invest 128:2894-2913, 2018—published online Jun. 4, 2018) (Year: 2018).*
Seong et al (J Korean Med Sci 28:1703-1710, 2013) (Year: 2013).*
Clinical diagnostic imaging technology, Science and Technology Literature Publisher, pp. 48-51, 2017 (see concise explanation of relevance, submitted separately).
International Search Report (w/ English translation) & Written Opinion for corresponding PCT Application No. PCT/JP2019/017963 dated Jun. 11, 2019, 6 pages.
Hori, et al, "Megalin Blockade with Cilastatin Suppresses Drug-Induced Nephrotoxicity," J Am Soc Nephrol, 2017, vol. 28(6), pp. 1783-1791.
Oyama, et al., "Evidence for megalin-mediated proximal tubular uptake of L-FABP, a carrier of potentially nephrotoxic molecules," Laboratory Investigation, 2005, vol. 85, pp. 522-531.
Christensen, et al., "Megalin and Cubilin: Multifunctional Endocytic Receptors," Nature Reviews Molecular Cell Biology, Apr. 2002, vol. 3, pp. 258-268.
Marzolo, et al., "New Insights into the Roles of Megalin/LRP2 and the Regulation of its Functional Expression," Biological Research, 2011, vol. 44, pp. 89-105.
Stacul, et al. "Contrast induced nephropathy: updated ESUR Contrast Media Safety Committee guidelines" *Eur. Radiol.* 21 (2011) pp. 2527-2541.
EPO. "Extended European Search Report" *Eur. Patent Ofc.* 19794059.6 (May 3, 2021) pp. 1-5.
Andreucci, et al. "The Choice of the Iodinated Radiographic Contrast Media to Prevent Contrast-Induced Nephropathy" *Adv. in Nephr.* 2014:691623 (2014) pp. 1-11.
Aspelin, et al. "Nephrotoxic Effects in High-Risk Patients Undergoing Angiography" *New Engl. J. Med.* 348 (2003) pp. 491-499.
Gomi, et al. "Are there any differences in acute adverse reactions among five low-osmolar non-ionic iodinated contrast media?" *Eur. Radiol.* 20 (2010) pp. 1631-1635.
Itoh, et al. "Involvement of de novo ceramide synthesis in radiocontrast-induced renal tubular cell injury" *Kidney Int'l.* 69 (2006) pp. 288-297.
Katayama, et al. "Iomeprol: Current and Future Profile of a Radiocontrast Agent" *Invest. Radiol.* 36 (2001) pp. 87-96.
Seeliger, et al. "Contrast Media Viscosity versus Osmolality in Kidney Injury: Lessons from Animal Studies" *BioMed Res. Int'l* 2014:358136 (2014) pp. 1-15.
Solomon, et al. "Cardiac Angiography in Renally Impaired Patients (CARE) Study" *Circulation* 115 (2007) pp. 3189-3196.

* cited by examiner

*Primary Examiner* — Craig D Ricci
(74) *Attorney, Agent, or Firm* — Dority & Manning, P.A.

(57) ABSTRACT

One object of the present invention is to provide an inhibitor for renal injuries induced by an iodinated contrast medium. In this invention, cilastatin or a pharmaceutically acceptable salt thereof is used.

7 Claims, 28 Drawing Sheets

Renal KIM-1 immunostaining in contrast nephropathy model

Renal PAS staining in contrast nephropathy model
(Observation of vacuole formation in renal proximal tubular epithelial cells)

Comparison of averaged X-ray count ratio in cortex between iomeprol contrast medium (CM) + cilastatin (CS)-treated group and CM + normal saline (NS)-treated group Mean ± SD     * $P<0.05$ (t-test)

Comparison of averaged X-ray count ratio in cortex between ioversol contrast medium (CM) + cilastatin (CS)-treated group and CM + normal saline (NS)-treated group Comparison of averaged X-ray count ratio in cortex between iodixanol contrast medium (CM) + cilastatin (CS)-treated group and CM + normal saline (NS)-treated group Mean ± SD  * $P<0.05$ (t-test)

Comparison of urinary KIM-1 levels between contrast medium (CM) + cilastatin (CS)-treated group and CM + normal saline (NS)-treated group Mean ± SD  * $P<0.05$ (t-test)

Verification of direct binding between iodinated contrast medium and megalin

Verification of binding between contrast and carrier protein

Comparison of averaged X-ray count ratio in cortex between iopamidol contrast medium (CM) + cilastatin (CS)-treated group and CM + normal saline (NS)-treated group

UTILIZATION OF CILASTATIN IN INHIBITING RENAL DISORDER

TECHNICAL FIELD

The present invention relates to utilization of cilastatin in inhibition of renal injuries. More specifically, this invention relates to an inhibitor for renal injuries induced by iodinated contrast media, the inhibitor comprising cilastatin or a pharmaceutically acceptable salt thereof.

BACKGROUND ART (Contrast Media)

Radiographic contrast techniques are of particularly important significance in clinical applications, including identification of pathological conditions and determination of therapeutic strategies. However, unlike bones, soft tissues are difficult to visualize because attenuation of X-rays is low in soft tissues. It is known that attenuation of X-rays is proportional to the density of a material and to the cube of the atomic number of an element constituting the material. Much interest has been focused on the use of iodine compounds in the development of transvascularly used contrast media. Such contrast media comprising an iodine compound as an active component are called iodinated contrast media.

All materials currently used as water-soluble contrast media have a triiodobenzene ring as a backbone. There are two types of contrast media having this backbone: ionic and nonionic. Ionic contrast media are known to increase osmotic pressure at the same iodine concentration, causing various side effects such as vascular pain, and thus are not approved for intravascular use in Japan.

Nonionic contrast media are developed for the purpose of ensuring enhanced safety through reduction of osmotic pressure. Representative examples of transvascularly used nonionic contrast media include, but are not limited to, ioxilan, iopromide, iohexol, ioversol, and iomeprol. Since these contrast media are almost the same in molecular weight and iodine content per unit volume, the degrees of X-ray attenuation (contrast effects) of these contrast media are considered nearly comparable. Further, for the purpose of reducing the number of molecules per unit iodine content, dimeric contrast media having two triiodobenzene rings in the molecule, such as iotrolan and iodixanol, are developed, whereby the physical property described as isosmoticity is achieved.

One of known severe side effects of contrast media is contrast nephropathy. Therefore, there is concern about the onset and progression of nephropathy. Further, in some patients with reduced renal function, the use of a contrast medium is in principle contraindicated and thus has to be abandoned.

Possible mechanisms for the onset of contrast-induced renal injuries include decreased renal blood flow and renal medullary hypoxia due to vasoconstriction, and damages caused by active oxygen. Therefore, many clinical studies have been performed in hopes of determining whether N-acetylcysteine or statin having antioxidant activity, or hANP having vasodilatory and renal blood flow enhancing activities, is capable of preventing the onset of contrast-induced nephropathy, but none of these agents were proved to be effective for such injuries.

The only currently recommended method of preventing contrast-induced renal injuries is intravenous administration of isotonic fluids such as normal saline or sodium bicarbonate fluid before and after contrast examination (NPL 1). However, the effectiveness of this preventive method is not supported by a high level of evidence.

(Megalin)

Megalin is a cell membrane protein also called LRP2 (low density lipoprotein (LDL)-receptor related protein 2) or gp330 (glycoprotein 330), and is a large, single-transmembrane glycoprotein having a molecular weight of about 600 kDa.

This protein functions as an endocytosis receptor and internalizes a substance (megalin ligand) bound to the megalin extracellular domain into cells. In mammals, megalin is observed to be expressed in renal proximal tubular epithelial cells (mainly luminal plasmalemma), inner ear epithelial cells, testis, neural ectoderm, and the like. In renal proximal tubular epithelial cells, glomerular-filtered proteins, administered drugs, or the like are bound to the extracellular domain of megalin and internalized into the cells by endocytosis (refer to e.g., NPLs 2, 3). For example, megalin-mediated endocytosis in renal proximal tubular epithelial cells plays a role in resorbing biological substances into the renal proximal tubules, thereby preventing the biological substances from being lost from the body.

There are different pathways that are involved in the mechanisms of the onset of renal injuries, and the megalin-mediated reabsorption mechanism is also known to contribute to the onset of renal injuries. To cite some examples, it is shown that the cyclic polypeptide antibiotic polymyxin B is bound to megalin and internalized into cells by endocytosis, thereby causing cellular injuries. Also, it is reported that aminoglycosidic antibiotics like gentamycin are bound to megalin and internalized into cells by endocytosis, but that combined administration of the aminoglycosidic antibiotics with a megalin ligand such as lysozyme, aprotinin or cytochrome C suppresses the nephrotoxicity of the antibiotics (refer to e.g., PTL 1).

It is found that when a megalin ligand functions as a carrier for a different substance, the substance bound to the carrier is absorbed into cells through megalin, thereby possibly causing cellular injuries or tissue injuries. For example, it is reported that fatty acids bound to liver-type fatty acid binding protein (L-FABP) may exert nephrotoxic effects (NPL 4). In other words, substances inducing renal injuries through the mediation of megalin are grouped into two types: substances directly bound to megalin and absorbed into cells, and substances absorbed into cells accompanying a megalin ligand.

(Cilastatin)

Cilastatin has inhibitory activity against DHP-I (dehydropeptidase-I) which is a metabolic enzyme present in renal proximal tubular brush-border membranes. Cilastatin is clinically used with the carbapenem-based antibiotic imipenem for the purpose of preventing inactivation of imipenem by DHP-I.

Cilastatin has been reported to have various activities. For example, PTL 2 discloses an inhibitor for megalin-mediated renal injuries, comprising cilastatin.

PTL 3 reports that cilastatin reduces nephrotoxicity induced by several drugs. This literature suggests that cilastatin may reduce nephrotoxicity through inhibition of the intracellular transport pathway through cholesterol rafts. These several drugs include particular types of contrast media (refer to e.g., Table 2).

CITATION LIST

Patent Literatures

PTL 1: Japanese Unexamined Patent Application Publication No. JP 2003-261459

PTL 2: International Patent Publication No. WO 2015/111666
PTL 3: U.S. Pat. No. 9,216,185

Non Patent Literatures

NPL 1: *Guidelines on the Use of Iodinated Contrast Media in Patients with Kidney Disease* 2012, JSN, JRS and JCS Joint Working Group, p. 50-79
NPL 2: Marzolo, et al., *Biological Research.* 2011, vol. 44, p. 89-105
NPL 3: Christensen, et al., *Nature Reviews Molecular Cell Biology,* 2002, vol. 3, p. 258-268
NPL 4: Oyama, et al., *Laboratory Investigation,* 2005, vol. 85, p. 522-531

SUMMARY OF INVENTION

Technical Problem

It can be expected that inhibition of binding of iodinated contrast media causing cellular injuries to megalin results in inhibition of intracellular internalization of the contrast media, leading to reduction of cellular injuries in the kidney.
An object of the present invention is to provide an inhibitor for contrast-induced renal injuries.

Solution to Problem

The present inventors have conducted intensive studies to achieve the aforementioned object and as a result found that cilastatin is effective for inhibition of renal injuries induced by iodinated contrast media.
The present invention includes, but is not limited to, the following embodiments.
1. An inhibitor for renal injuries induced by an iodinated contrast medium, the inhibitor comprising cilastatin or a pharmaceutically acceptable salt thereof as an active component (except the case where the iodinated contrast medium is iopamidol).
2. The inhibitor as set forth in 1, wherein the iodinated contrast medium is selected from the group consisting of compounds having a chemical structure containing one or more 2,4,6-triiodophenyl groups in which the 3 position and/or the 5 position is optionally substituted by a substituent, and pharmaceutically acceptable salts thereof.
3. The inhibitor as set forth in 1 or 2, wherein the iodinated contrast medium is nonionic.
4. The inhibitor as set forth in any of 1 to 3, wherein the iodinated contrast medium is selected from the group consisting of ioxilan, iopromide, iohexol, ioversol, iomeprol, iotrolan, iodixanol, ioxaglic acid, iotroxic acid, amidotrizoic acid, iotalamic acid, and pharmaceutically acceptable salts thereof.
5. The inhibitor as set forth in any of 1 to 4, wherein the iodinated contrast medium is selected from the group consisting of ioxilan, iopromide, iohexol, ioversol, iomeprol, iodixanol, ioxaglic acid, and pharmaceutically acceptable salts thereof, selected from the group consisting of ioversol, iomeprol, iodixanol, and pharmaceutically acceptable salts thereof, or selected from the group consisting of iomeprol, iodixanol, and pharmaceutically acceptable salts thereof.
6. The inhibitor as set forth in any of 1 to 5, wherein the inhibitor is in an injectable form.
(A1) Use of cilastatin or a pharmaceutically acceptable salt thereof in the inhibition of renal injuries induced by an iodinated contrast medium (except the case where the iodinated contrast medium is iopamidol).
(A2) The use as set forth in A1, wherein the iodinated contrast medium is selected from the group consisting of compounds having a chemical structure containing one or more 2,4,6-triiodophenyl groups in which the 3 position and/or the 5 position is optionally substituted by a substituent, and pharmaceutically acceptable salts thereof.
(A3) The use asset forth in A1 or A2, wherein the iodinated contrast medium is nonionic.
(A4) The use as set forth in any of A1 to A3, wherein the iodinated contrast medium is selected from the group consisting of ioxilan, iopromide, iohexol, ioversol, iomeprol, iotrolan, iodixanol, ioxaglic acid, iotroxic acid, amidotrizoic acid, iotalamic acid, and pharmaceutically acceptable salts thereof.
(A5) The use as set forth in any of A1 to A4, wherein the iodinated contrast medium is selected from the group consisting of ioxilan, iopromide, iohexol, ioversol, iomeprol, iodixanol, ioxaglic acid, and pharmaceutically acceptable salts thereof, selected from the group consisting of ioversol, iomeprol, iodixanol, and pharmaceutically acceptable salts thereof, or selected from the group consisting of iomeprol, iodixanol, and pharmaceutically acceptable salts thereof.
(A6) The use asset forth in any of A1 to A5, wherein the cilastatin or the pharmaceutically acceptable salt thereof is used in an injectable form.
(B1) A method for inhibiting renal injuries induced by an iodinated contrast medium, the method comprising administering an effective amount of cilastatin or a pharmaceutically acceptable salt thereof to a subject in need thereof (except the case where the iodinated contrast medium is iopamidol).
(B2) The method asset forth in B1, wherein the iodinated contrast medium is selected from the group consisting of compounds having a chemical structure containing one or more 2,4,6-triiodophenyl groups in which the 3 position and/or the 5 position is optionally substituted by a substituent, and pharmaceutically acceptable salts thereof.
(B3) The method as set forth in B1 or B2, wherein the iodinated contrast medium is nonionic.
(B4) The method asset forth in any of B1 to B3, wherein the iodinated contrast medium is selected from the group consisting of ioxilan, iopromide, iohexol, ioversol, iomeprol, iotrolan, iodixanol, ioxaglic acid, iotroxic acid, amidotrizoic acid, iotalamic acid, and pharmaceutically acceptable salts thereof.
(B5) The method as set forth in any of B1 to B4, wherein the iodinated contrast medium is selected from the group consisting of ioxilan, iopromide, iohexol, ioversol, iomeprol, iodixanol, ioxaglic acid, and pharmaceutically acceptable salts thereof, selected from the group consisting of ioversol, iomeprol, iodixanol, and pharmaceutically acceptable salts thereof, or selected from the group consisting of iomeprol, iodixanol, and pharmaceutically acceptable salts thereof.
(B6) The use asset forth in any of B1 to B5, wherein the cilastatin or the pharmaceutically acceptable salt thereof is administered in an injectable form.

Advantageous Effects of Invention

The present invention can inhibit renal injuries induced by an iodinated contrast medium (except the case where the iodinated contrast medium is iopamidol). For example, this invention can inhibit renal injuries characterized by cellular injuries induced by an iodinated contrast medium through the mediation of megalin, or namely, renal injuries induced by an iodinated contrast medium through the mediation of megalin. Moreover, cilastatin or a pharmaceutically acceptable salt thereof can be administered relatively safely. Therefore, this invention makes it possible to use an iodinated contrast medium while avoiding diseases such as renal injuries.

In connection with the present invention, it is found that intracellular absorption of an iodinated contrast medium through megalin is caused not by direct binding of the contrast medium to megalin but by binding of them through a certain type of carrier. Therefore, it is considered that cilastatin inhibits renal injuries through inhibition of indirect binding of an iodinated contrast medium.

As used herein in connection with renal injuries, the term "inhibit (inhibiting or inhibition)" refers to, for example, complete prevention of the onset of a symptom caused by an iodinated contrast medium, reduction of a symptom as compared to when using an iodinated contrast medium alone, or enabling use of an iodinated contrast medium in a subject in which use of an iodinated contrast medium has been abandoned due to a previously existing symptom. The term "reduction" as referred to above includes decreasing the severity of the symptom, and complete elimination of the symptom. For the purpose of the specification, complete prevention of the onset of a disease symptom, or reduction of a symptom as compared to when using a contrast medium alone, is referred to as "prevention", and also included in the scope of the term "inhibition". Further, a medicament for "inhibiting" renal injuries may also be referred to as an "inhibitor".

DESCRIPTION OF EMBODIMENTS (Cilastatin)

Figure 1:
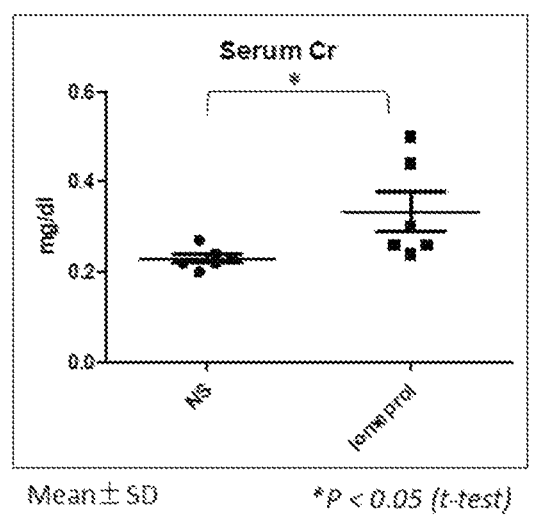
FIG. 1 shows a graph that compares serum creatinine levels between the iodinated contrast medium (iomeprol)-treated group and the control group.

In the present invention, cilastatin or a pharmaceutically acceptable salt thereof is used.

Cilastatin refers to (Z)-7-[[(R)-2-amino-2-carboxyethyl]thio]-2-[[[(S)-2,2-dimethylcyclopropyl]carbonyl]amino]-2-heptenoic acid. For the sake of confirmation, when cilastatin produces a hydrate, use of the hydrate of cilastatin is also included within the scope of this invention.

Examples of a pharmaceutically acceptable salt of cilastatin include, but are not limited to, alkali metal salts, such as lithium salt, sodium salt and potassium salt; alkali earth metal salts, such as magnesium salt and calcium salt; zinc salt and aluminum salt: organic amine salts, such as choline salt, ethanolamine salt, trimethylamine salt, triethylamine salt, dicyclohexylamine salt, dibenzylamine salt, phenethylbenzylamine salt, procaine salt, morpholine salt, pyridine salt, piperidine salt, piperadine salt and N-ethylpiperidine salt: ammonium salt; basic amino acid salts, such as lysine salt and arginine salt. A particularly preferred salt is cilastatin sodium. For the sake of confirmation, the scope of pharmaceutically acceptable salts also includes hydrates of the salts.

As cilastatin or a pharmaceutically acceptable salt thereof, use can be made of, for example, a commercially available product, or a product produced and obtained by a per se known method or by a method pursuant to a known method.

Cilastatin binds to the extracellular domain of megalin. Cilastatin or a pharmaceutically acceptable salt thereof is capable of inhibiting indirect binding of an iodinated contrast medium to megalin and intracellular internalization of an iodinated contrast medium.

(Iodinated Contrast Medium)

In the present invention, renal injuries induced by iodinated contrast media are inhibited by cilastatin or a pharmaceutically acceptable salt thereof. The iodinated contrast medium is selected from compounds having a chemical structure containing one or more (preferably one, two or three, more preferably one or two, still more preferably one) 2,4,6-triiodophenyl groups in which the 3 position and/or the 5 position is optionally substituted by a substituent, and pharmaceutically acceptable salts thereof. The iodinated contrast medium is preferably nonionic. As referred to above, the "nonionic contrast medium" refers to a contrast medium having no ionic functional group. A typical ionic functional group is a carboxyl group. Examples of nonionic iodinated contrast media include ioxilan, iopamidol, iopromide, iohexol, ioversol, iomeprol, iotrolan, iodixanol, and pharmaceutically acceptable salts thereof. The iodinated contrast medium is preferably selected from the group consisting of ioxilan, iopromide, iohexol, ioversol, iomeprol, iotrolan, iodixanol, ioxaglic acid, iotroxic acid, amidotrizoic acid, iotalamic acid, and pharmaceutically acceptable salts thereof, more preferably selected from the group consisting of ioxilan, iopromide, iohexol, ioversol, iomeprol, iotrolan, iodixanol, ioxaglic acid, iotroxic acid, amidotrizoic acid, iotalamic acid, and pharmaceutically acceptable salts thereof, and still more preferably selected from the group consisting of ioxilan, iopromide, iohexol, ioversol, iomeprol, iodixanol, ioxaglic acid, and pharmaceutically acceptable salts thereof. Another example of a preferred iodinated contrast medium is selected from the group consisting of iomeprol, iohexol and pharmaceutically acceptable salts thereof. Still another example of a preferred iodinated contrast medium is selected from the group consisting of ioversol, iomeprol, iodixanol, and pharmaceutically acceptable salts thereof. Yet another example of a preferred iodinated contrast medium is selected from the group consisting of iomeprol, iodixanol, and pharmaceutically acceptable salts thereof. For the sake of confirmation, when a free form of an iodinated contrast medium produces a hydrate, use of such a hydrate is also included within the scope of this invention.

Examples of pharmaceutically acceptable salts of the aforementioned compounds include the following: when the aforementioned compounds have a carboxyl group, base addition salts formed at the carboxyl group; and when the aforementioned compounds have an amino group, an imino group, a basic heterocyclic group, or other group containing a basic nitrogen atom, acid addition salts formed at the basic nitrogen atom.

Examples of the base addition salts include alkali metal salts, such as lithium salt, sodium salt and potassium salt; alkali earth metal salts, such as calcium salt and magnesium salt; zinc salt and aluminum salt; ammonium salt; and organic amine salts, such as meglumine salt, choline salt, ethanolamine salt, trimethylamine salt, triethylamine salt, dicyclohexylamine salt, diethanolamine salt, triethanolamine salt, morpholine salt, pyridine salt, piperidine salt, piperadine salt, procaine salt, and N,N'-dibenzylethylenediamine salt. Two or more of the aforementioned base addition salts may be used in combination.

Examples of the acid addition salts include inorganic acid salts, such as sulfate, chloride, hydrobromide, nitrate, phosphate, and perchlorate; organic acid salts, such as formate, acetate, trifluoroacetate, oxalate, lactate, maleate, fumarate, tartrate, citrate, and ascorbate; and sulfonates, such as methanesulfonate, isetionate, benzenesulfonate, p-toluenesulfonate, and camphorsulfonate. Two or more of the aforementioned acid addition salts may be used in combination.

For the sake of confirmation, the scope of pharmaceutically acceptable salts also includes hydrates of the salts.

As the iodinated contrast medium, use can be made of, for example, a commercially available product, or a product produced and obtained by a per se known method or by a method pursuant to a known method.

(Inhibitor)

In one aspect, the present invention is directed to an inhibitor for renal injuries induced by an iodinated contrast medium, the inhibitor comprising cilastatin or a pharmaceutically acceptable salt thereof as an active component. Specific examples of iodinated contrast media, and examples of a preferred iodinated contrast medium are as mentioned above.

Renal injuries can be induced by an iodinated contrast medium through the mediation of megalin. Since the main site of expression of megalin in the body is renal proximal tubular epithelial cells (mainly luminal plasmalemma), cilastatin or a pharmaceutically acceptable salt thereof is useful (i.e., as an inhibitor) for the inhibition of renal proximal tubular epithelial cell injury induced by an iodinated contrast medium through the mediation of megalin, and renal injuries derived therefrom.

Examples of renal injuries induced by iodinated contrast media include contrast(-induced) nephropathy, contrast(-induced) renal injury, contrast(-induced) nephritis, contrast (-induced) renal failure, contrast(-induced) renal disease, drug(-induced) nephropathy, drug(-induced) renal injury, drug(-induced) nephritis, drug(-induced) renal failure, drug (-induced) renal disease, acute nephropathy, acute renal injury, acute nephritis, acute renal failure, acute renal disease, chronic nephropathy, chronic renal injury, chronic nephritis, chronic renal failure, chronic renal disease, tubular nephropathy, tubular renal injury, tubular nephritis, tubular renal failure, tubular renal disease, tubulointerstitial nephropathy, tubulointerstitial renal injury, tubulointerstitial nephritis, tubulointerstitial renal failure, tubulointerstitial renal disease, obstructive nephropathy, obstructive renal injury, obstructive nephritis, obstructive renal failure, obstructive renal disease, acute nephritic syndrome, rapidly progressive nephritic syndrome, chronic nephritic syndrome, nephrotic syndrome, renal vasospasm, and acute tubular necrosis. The present invention is also useful for the inhibition of other diseases or symptoms than drug-induced renal injuries.

In a preferred embodiment, the inhibitor of this invention does not comprise imipenem.

(Dose of Active Component)

The dose of the inhibitor of the present invention can be such a dose that cilastatin or a pharmaceutically acceptable salt thereof can be provided in an effective amount for inhibiting renal injuries induced by an iodinated contrast medium. For the purpose of inhibition of renal injuries, an exemplary daily dose of cilastatin or a salt thereof in an adult is from 1.0 to 2.0 g, or from 1.0 to 1.5 g. To achieve such a dose, the inventive inhibitor can be administered once or in divided doses. The inhibitor may also be administered using an intermittent dosing regimen, such as alternate-day or every three day regimen.

The iodinated contrast medium can be used in combination with cilastatin or a pharmaceutically acceptable salt thereof. In such a case, the course of therapy with an iodinated contrast medium to be combined is not particularly limited, and can be determined by those skilled in the art depending on the need by reference to known literatures or the like. For example, the package insert of "Iomeron®" produced by Bracco-Eisai Co., Ltd., which is a contrast medium product whose generic name is "iomeprol", states as follows regarding its usage.

TABLE 1

Single doses for adults (These doses can be increased or decreased as appropriate depending on the age, body weight, symptom and purpose.)

| Type of imaging | | Dosage regimen/ Iodine content in injectable formulation | | |
|---|---|---|---|---|
| | | 300 mg/mL | 350 mg/mL | 400 mg/mL |
| Cerebral blood vessel angiography | | 5-15 mL | — | — |
| Angiocardiography | Intracardiac angiography | — | 20-50 mL | 20-40 mL |
| | Coronary arterial angiography | — | 3-10 mL | 3-8 mL |
| Thoracic angiography | | 5-50 mL | 5-50 mL | 5-50 mL |
| Abdominal angiography | | 5-60 mL | 5-60 mL | 5-60 mL |
| Extremities angiography | | 10-80 mL | 10-80 mL | — |
| Digital radiography | Venous angiography | 10-50 mL | 10-50 mL | — |
| | Arterial angiography | 3-40 mL | 3-40 mL | — |
| Computer-assisted tomography (CT) | | 40-100 mL | 40-100 mL | — |
| Intravenous urography | | 40-100 mL | 30-100 mL | 50 mL |

The total dose of multiple treatments is up to 250 mL.
For dynamic computer-assisted tomography of the liver region, the maximum dose based on weight is 135 mL (350 mg/mL formulation).

(Dosage Form)

The form of the inhibitor of the present invention is not particularly limited, and the inhibitor of this invention can be in the form of, for example, a solid formulation such as powder, granule, capsule, tablet or chewable tablet, a liquid formulation such as solution or syrup, or an injectable, or a spray. A preferred form of the inhibitor is an injectable.

The inhibitor of the present invention may contain a pharmaceutically acceptable carrier when required for pharmaceutical purposes. Examples of such a carrier include, for example, excipient and solvent. Examples of additional components that may be contained in the inhibitor of this invention include binder, pH adjustor, disintegrant, chelator, solubilizer, suspending agent, emulsifier, isotonizer, solubilizer, soothing agent, antiseptic, antioxidant, lubricant, corrigent, and colorant.

Examples of excipients include, but are not limited to, organic excipients, such as sugars like lactose, glucose and D-mannitol, starches, and celluloses like crystalline cellulose; and inorganic excipients, such as dicalcium phosphate, calcium carbonate and kaolin. Examples of solvents include, but are not limited to, purified water and normal saline. Examples of binders include, but are not limited to, pregelatinized starch, gelatin, gum Arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, and polyvinyl alcohol. Examples of pH adjustors include, but are not limited to, hydrochloric acid and sodium hydroxide. Examples of disintegrants include, but are not limited to, low-substituted hydroxypropylcellulose, chemically modified celluloses and starches, and alginic acid. Examples of chelators include, but are not limited to, calcium disodium edetate hydrate and calcium sodium edetate hydrate. Examples of solubilizers include, but are not limited to, polyethylene glycol, propylene glycol, trehalose, benzyl benzoate, ethanol, sodium carbonate, sodium citrate, sodium salicylate and sodium acetate. Examples of suspending agents or emulsifiers include, but are not limited to, sodium lauryl sulfate, gum Arabic, gelatin, lecithin, glyceryl monostearate, polyvinyl alcohol, polyvinylpyrrolidone, celluloses like carboxymethylcellulose sodium, polysorbates, and polyoxyethylene hydrogenated castor oil. Examples of isotonizers include, but are not limited to, sodium chloride, potassium chloride, sugars, glycerin, and urea. Examples of stabilizers include, but are not limited to, polyethylene glycol, sodium dextran sulfate, and other amino acids. Examples of soothing agents include, but are not limited to, glucose, calcium gluconate and procaine hydrochloride. Examples of antiseptics include, but are not limited to, p-hydroxybenzoic esters, chlorobutanol, benzyl alcohol, phenethyl alcohol, dehydroacetic acid, and sorbic acid. Examples of antioxidants include, but are not limited to, sulfite and ascorbic acid.

The content of cilastatin or a pharmaceutically acceptable salt thereof in the inhibitor of the present invention is not particularly limited, but is in the range of, for example, from 0.001 to 100% by mass, from 0.001 to 99.9% by mass, or from 0.01 to 90% by mass.

When the inhibitor of the present invention is an injectable, the injectable may be in a solution form in which an active component and the like are dissolved beforehand, or in a solid form which is to be dissolved just before use. It is preferred that the injectable solution should comprise cilastatin or a pharmaceutically acceptable salt thereof as an active component at a concentration of, for example, from 0.001 to 10% by mass, from 0.01 to 5% by mass, or from 0.1 to 1% by mass, based on the mass of the entire solution. When the inhibitor is in a solid form which is to be dissolved upon use, the content of cilastatin or a pharmaceutically acceptable salt thereof in the inhibitor is in the range of, for example, from 0.001 to 100% by mass, from 0.001 to 99.9% by mass, or from 0.01 to 90% by mass. An appropriate solvent or diluent to make an injectable solution can be any commonly used one, and examples thereof include aqueous media such as normal saline, injectable distilled water, aqueous glucose solution, aqueous lidocaine hydrochloride solution (for intramuscular injection), intravenous injection fluid (e.g., aqueous solution of citric acid, sodium citrate or the like) and electrolyte solution (for intravenous drip infusion and intravenous injection), organic media such as ethanol, polyethylene glycol and propylene glycol, or mixtures thereof.

(Method and Use)

In another aspect, the present invention is directed to use of cilastatin or a pharmaceutically acceptable salt thereof in the inhibition of renal injuries induced by an iodinated contrast medium (except the case where the iodinated contrast medium is iopamidol). Specific examples of iodinated contrast media, examples of a preferred iodinated contrast medium, and examples of a preferred renal injury are as mentioned above. Said use may be further combined with administration of an effective amount of an iodinated contrast medium. The iodinated contrast medium can be administered simultaneously with, separately from or at a time interval from, cilastatin or a pharmaceutically acceptable salt thereof. For example, the iodinated contrast medium may be administered simultaneously with, prior to, or after administration of cilastatin or a pharmaceutically acceptable salt thereof. Alternatively, two or more of these administration timings may be adopted in combination.

In another aspect, the present invention is directed to a method for inhibiting renal injuries induced by an iodinated contrast medium, the method comprising administering an effective amount of cilastatin or a pharmaceutically acceptable salt thereof to a subject in need thereof (except the case where the iodinated contrast medium is iopamidol). Specific examples of iodinated contrast media, examples of a preferred iodinated contrast medium, and examples of a preferred renal injury are as mentioned above. Said method may further comprise administering to the subject an effective amount of an iodinated contrast medium. The iodinated contrast medium can be administered simultaneously with, separately from, or at a time interval from, cilastatin or a pharmaceutically acceptable salt thereof. For example, the iodinated contrast medium may be administered simultaneously with, prior to, or after administration of cilastatin or a pharmaceutically acceptable salt thereof. Alternatively, two or more of these administration timings may be adopted in combination.

In the case of combined administration as mentioned above, individual components or agents can be administered as separate formulations or as a single formulation.

In a preferred embodiment, the method and use of the present invention does not comprise administering imipenem.

As referred to herein, the "subject in need thereof (i.e., of inhibiting renal injuries induced by an iodinated contrast medium)" refers to a subject having or at risk of having a symptom of a renal injury, and a subject contraindicated for treatment with an iodinated contrast medium because of the presence of said symptom before treatment. Said subject is preferably a mammal such as human, a domestic animal such as mouse, rat, rabbit, guinea pig, hamster, monkey, sheep, horse, cow, pig, donkey, dog or cat, or other laboratory animal, with a human being particularly preferred.

The doses of cilastatin or a pharmaceutically acceptable salt thereof and an iodinated contrast medium are as mentioned above in connection with the inhibitor of the present invention.

(Numerical Range)

For the sake of clarity, the numerical ranges defined herein by lower and upper limit values, like "from 1.0 to 2.0 g", include the lower and upper limit values.

EXAMPLES

Hereunder, the present invention will be described by way of examples, but this invention is not limited to these examples.

Among iodinated contrast media used, iomeprol was a Japanese Pharmacopeia iomeprol injectable solution ("Iomeront® 350" (Bracco-Eisai Co., Ltd.)), iohexol was a Japanese Pharmacopeia iohexol injectable solution ("Omnipaque® 350" (Daiichi Sankyo Co., Ltd.)), iopamidol was a Japanese Pharmacopeia iopamidol injectable solution ("Iopamiron®, 370" (Bayer Yakuhin, Ltd.)), iodixanol was the iodixanol injection "Visipaque® 320" (Daiichi Sankyo Co., Ltd.), ioversol was the ioversol injectable solution "Optiray® 350" (Fuji Pharma Co., Ltd.), and iopromide was an iopromide injectable solution ("Iopromide 370 Injection FRI" (FUJIFILM RI Pharma Co., Ltd./exporter: Bayer Yakuhin, Ltd.)). A cilastatin sample used was cilastatin sodium (Sigma-Aldrich Japan K.K.).

The animal species used were any of C57BL/6J (male, aged 9-12 weeks, Charles River Laboratories International), kidney-specific megalin complete knockout mice Ndrg1-CreERT2/+megalin lox/lox (male, aged 12 weeks) (hereinafter also referred to as "NDRG1-Cre"), and kidney-specific megalin partial knockout mice ApoE cre, megalin lox/lox (male, aged 12 weeks)(hereinafter also referred to as "apoE-Cre").

Reference Example 1

Murine models of contrast nephropathy were constructed.
Methodology

Left kidneys were extracted from C57BL/6J mice (male, aged 9-12 weeks, Charles River Laboratories International), and 14 days later, right kidney pedicles were ligated for 30 minutes. Thereafter, reperfusion was carried out. For the iomeprol-treated group, 200 µL of iomeprol was administered from the tail vein after 24 hours from the start of reperfusion. For the control group, 200 µL of normal saline instead of iomeprol was administered from the tail vein. After 48 hours from the administration, the animals in both groups were euthanized and evaluated.

For 24 hours before euthanization, urine samples were collected using a metabolic cage. Upon euthanization, blood samples were collected from the inferior vena cava, and then right kidneys were extracted. The collected blood samples were centrifuged for 30 minutes at 800 g at room temperature to separate and collect the serum. The obtained urine and serum samples were stored at −80° C. until analysis.

For biochemical evaluation of renal injuries, serum creatinine (Cr) and urea nitrogen (MN) levels, and urinary Cr and β-D-N-acetylglucosaminidase (NAG) were measured. Serum MN and Cr measurements were contracted to Oriental Yeast Co., Ltd., and urinary NAG and Cr measurements were to SRL, Inc.

For histological evaluation, 3 mm-thick sections containing a kidney pedicle portion were prepared from the above extracted right kidneys, fixed with 4% paraformaldehyde phosphate buffer, and sliced at a thickness of 4 µm using a microtome (REM-710; Yamato Kohki Industrial Co., Ltd.). The obtained thin slices were stained with periodic acid-Shiff (PAS) and immunostained with the renal injury marker Kidney Injury Molecule-1 (KIM-1). The immunostaining was performed using VECTASTAIN Elite ABC Kit (Vector Laboratories, Inc.).

Results

Figure 2:
FIG. 2 shows an image of immunostaining of an injured kidney tissue after iodinated contrast medium (iomeprol) treatment, using an antibody against the renal injury marker KIM-1.
Figure 3:
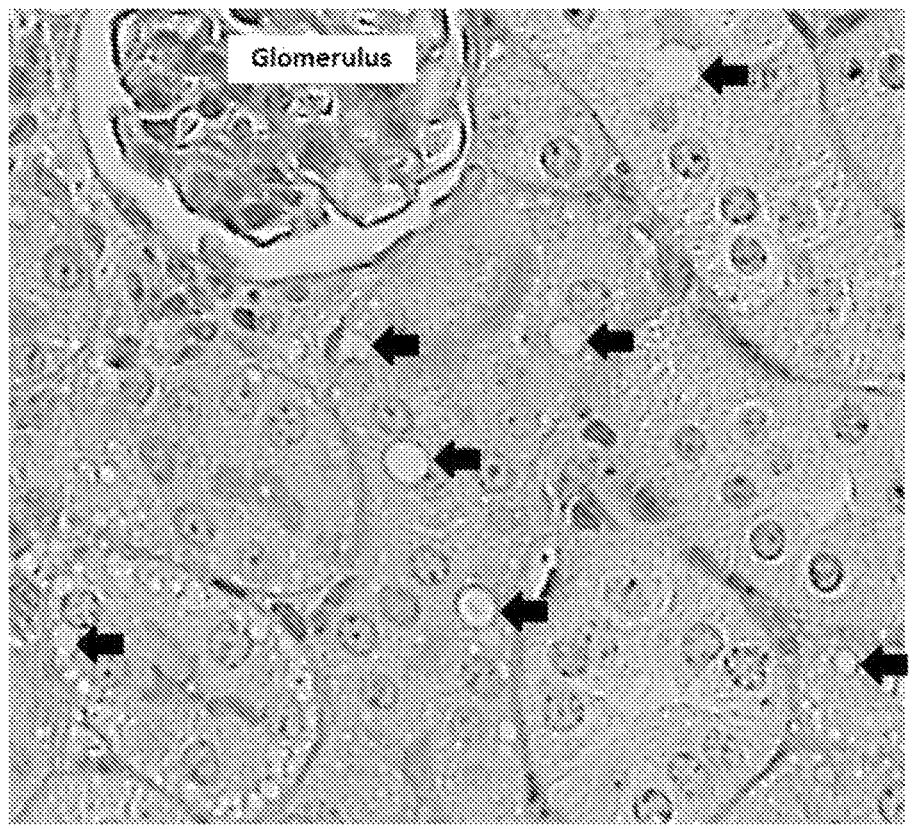
FIG. 3 shows an image of PAS staining of an injured kidney tissue after iodinated contrast medium (iomeprol) treatment.
Figure 4:
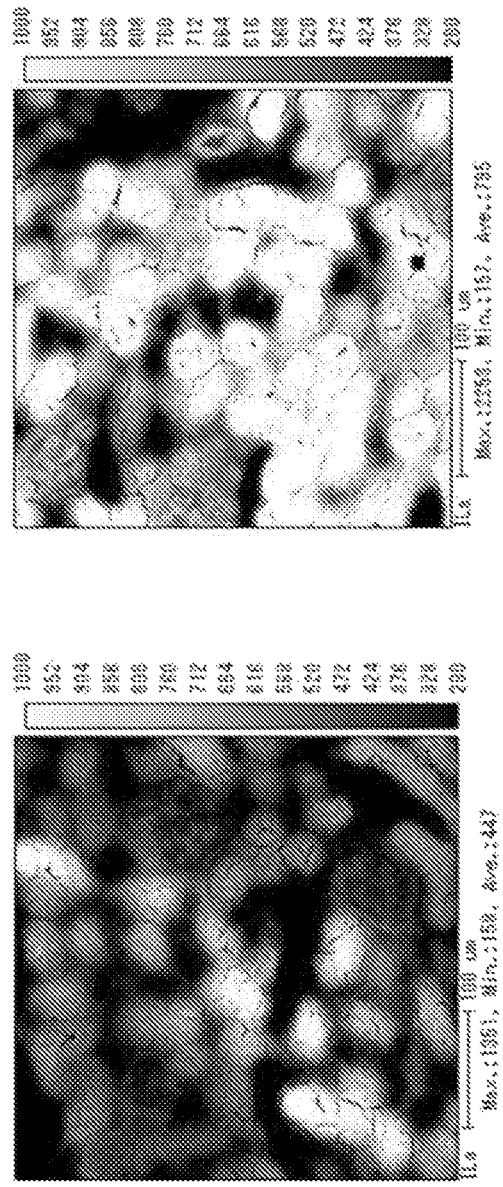
FIG. 4 shows the results of EMPA mapping of iodine in the kidney tissues of a kidney-specific megalin complete knockout mouse (NDRG1-Cre) and a control mouse after iodinated contrast medium (iomeprol) treatment.
Figure 5:
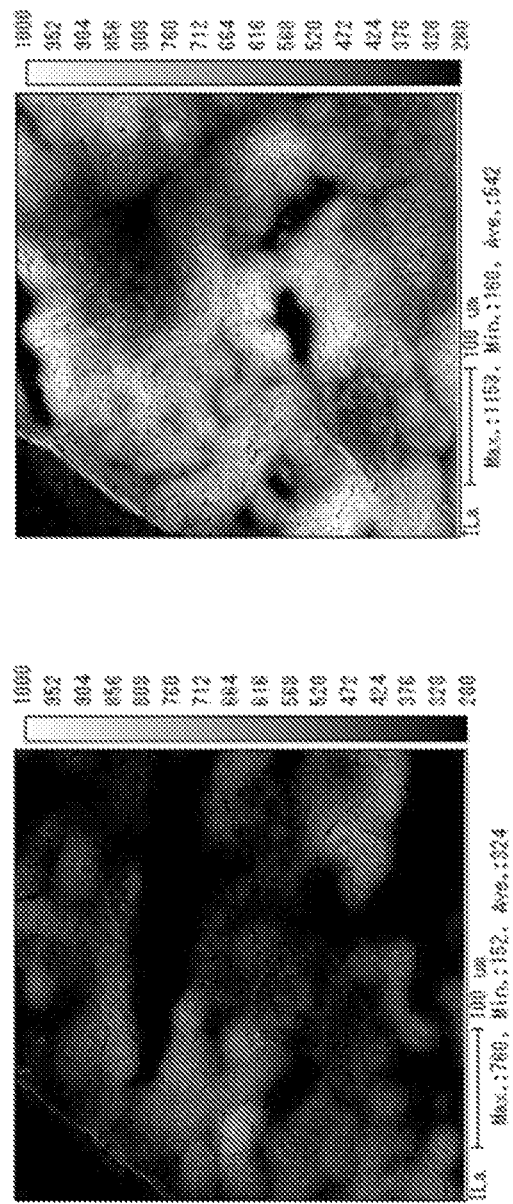
FIG. 5 shows the results of EMPA mapping of iodine in the kidney tissues of a kidney-specific megalin complete knockout mouse (NDRG1-Cre) and a control mouse after iodinated contrast medium (iohexol) treatment.
Figure 6:
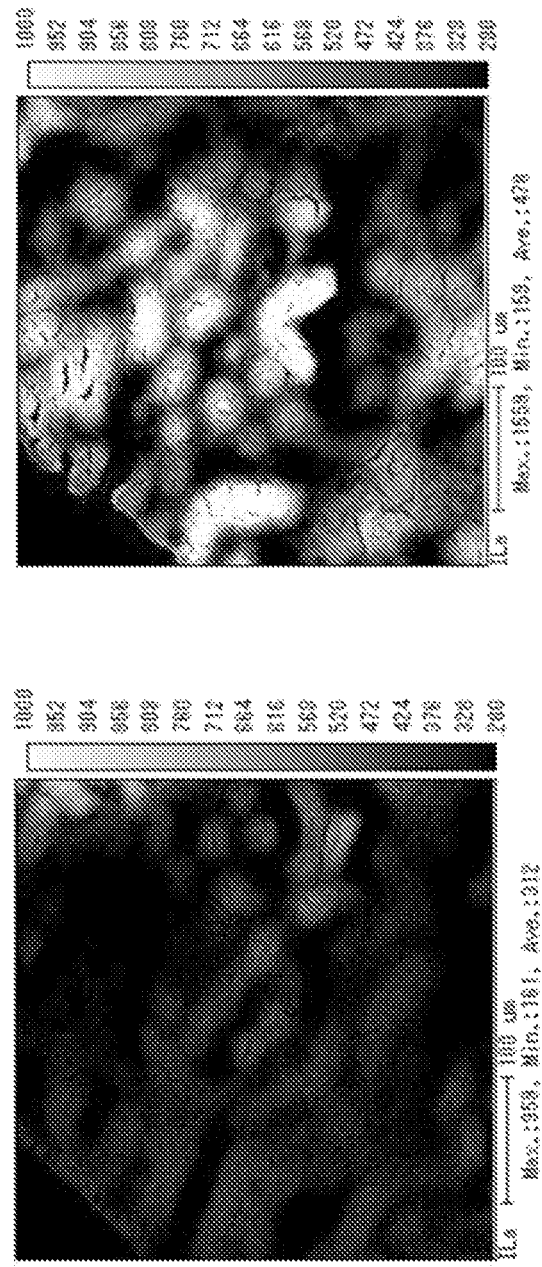
FIG. 6 shows the results of EMPA mapping of iodine in the kidney tissues of a kidney-specific megalin complete knockout mouse (NDRG1-Cre) and a control mouse after iodinated contrast medium (iopamidol) treatment.
Figure 7:
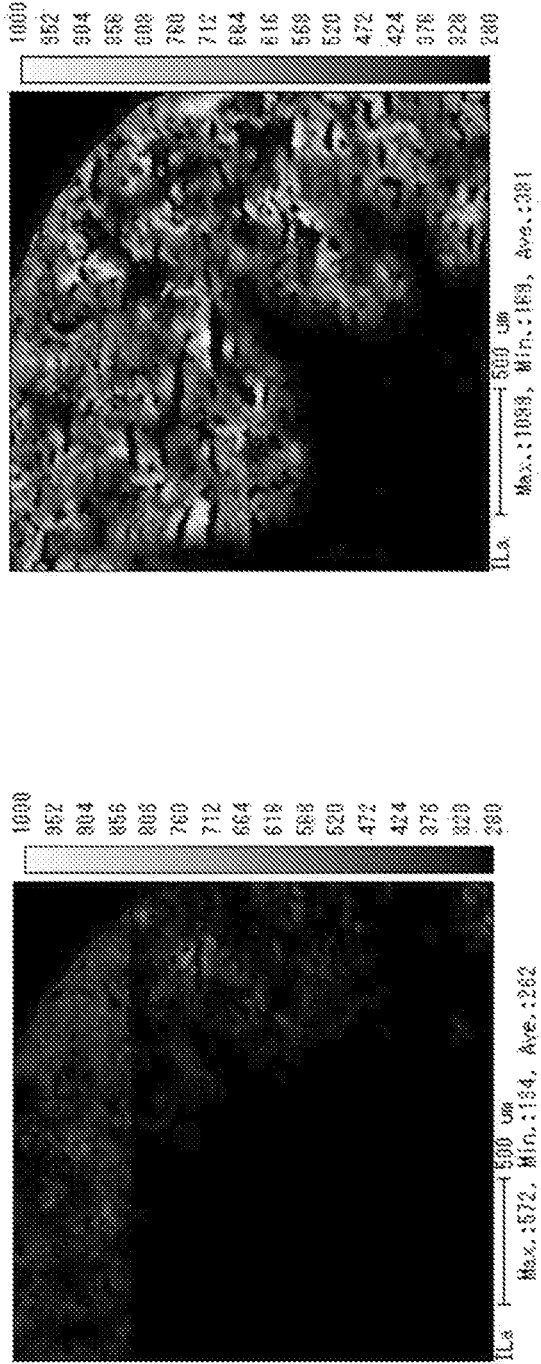
FIG. 7 shows the results of EMPA mapping of iodine in the kidney tissues of a kidney-specific megalin complete knockout mouse (NDRG1-Cre) and a control mouse after iodinated contrast medium (iopromide) treatment.
Figure 8:
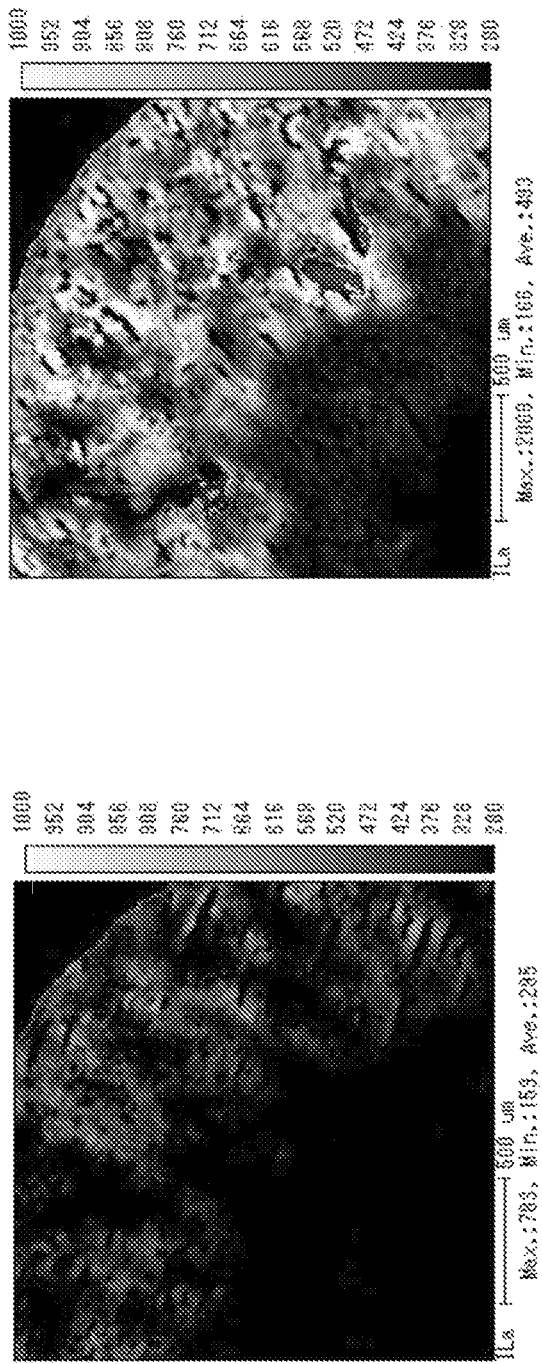
FIG. 8 shows the results of EMPA mapping of iodine in the kidney tissues of a kidney-specific megalin complete knockout mouse (NDRG1-Cre) and a control mouse after iodinated contrast medium (ioversol) treatment.
Figure 9:
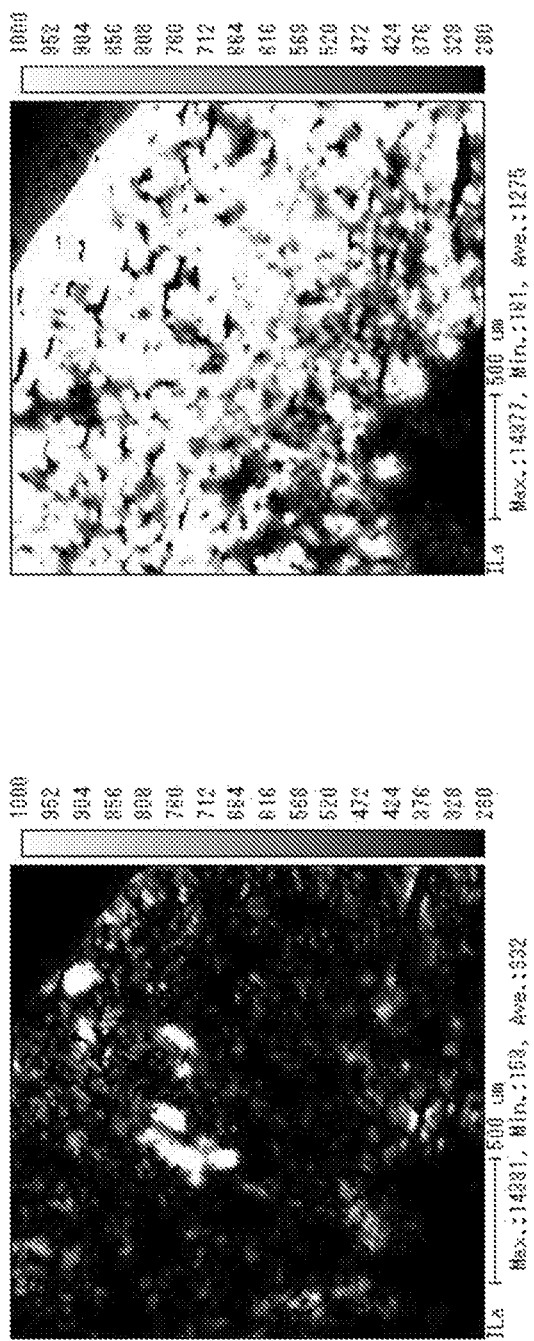
FIG. 9 shows the results of EMPA mapping of iodine in the kidney tissues of a kidney-specific megalin complete knockout mouse (NDRG1-Cre) and a control mouse after iodinated contrast medium (iodixanol) treatment.

The results are shown in FIGS. 1-3. There was a significant (t-test) increase in serum Cr in the iomeprol-treated ("Iomeprol") group as compared to the control ("NS") group (FIG. 1). From the histological viewpoint, KIM-1 was widely expressed mainly in the S1 and S2 segments of renal proximal tubular epithelial cells (circled portions in FIG. 2). Further, the formation of vacuoles was observed by PAS staining (as indicated by arrows in FIG. 3).

As a result of the biochemical and histological evaluations conducted above, it was confirmed that the models of contrast nephropathy were successfully constructed.

Reference Example 2

With the use of kidney-specific megalin complete knock-out mice NDRG1-Cre and their control mice (uninduced), it was verified by an electron probe microanalyzer (EPMA) that the absorption of contrast media (iodine) into renal proximal tubular epithelial cells was megalin dependent.

EPMA is an electron microprobe (EMP) instrument that analyzes the constituent elements of a substance of interest by irradiating electron beams onto the substance and measuring the wavelengths and intensities of characteristic X-rays unique to the different elements, which are generated by the electron beams. The presence of iodine in sections can be determined by EMP analysis (Nordby, et al., *Scanning Microsc*, 1990, vol. 4, p. 651-666). It has been found that contrast media are not metabolized in the body. The behaviors of contrast media per se can be verified by analyzing iodine content distribution.

The "thin-film quantification" technique can be applied for analysis of biological samples such as kidney tissue sections. During EPMA analysis, assuming that electron beam irradiation and X-ray detection are performed under the same conditions, the following relationship is established.

$$Ix=KNx$$

Ix: X-ray intensity
Nx: Number of atoms
K: Constant determined by instrument

Since the intensity of X-ray generated when a sample of interest is irradiated with an electron beam is proportional to the number of atoms present, comparison of X-ray intensity enables indirect comparison of the number of atoms.

Methodology

The NDRG1-Cre and control mice were administered with iomeprol, iohexol, iopamidol, iopromide, ioversol or iodixanol as a contrast medium, or with 200 µL of normal saline, from the tail vein, and 3 hours later, kidneys were extracted. In order to use right kidneys for analysis, 3 mm-thick sections containing a kidney pedicle portion were prepared, embedded in OCT compound, freeze-fixed with liquid nitrogen, and stored at −80° C.

Next, the stored sections were sliced at a thickness of 4 µm using a cryostat (CM1850, Leica Biosystems), and the obtained slices were attached onto carbon-coated grids and freeze-dried overnight.

378 µm$^2$ cortical areas in the prepared tissue slices were analyzed by EPMA (EPMA 1610, Shimadzu Corporation, Kyoto, Japan) to map iodine present in the structures of the contrast media.

Results

The results are shown in FIGS. 4-9. High concentrations of iodine were detected in all the kidney slices from the control mice administered with any of the iomeprol, iohexol, iopamidol, iopromide, ioversol and iodixanol contrast media (bright regions indicating high concentrations are larger in the images showing the results for the control mice in FIGS. 4-9), whereas the iodine contents detected were lower in the kidney slices from the NDRG1-Cre mice than in those from the control mice (dark regions indicating low concentrations are larger in the images showing the results for the NDRG1-Cre mice in FIGS. 4-9).

This experiment confirmed that internalization of contrast media was megalin dependent.

Reference Example 3

Similar murine models of contrast nephropathy to those of Reference Example 1 were constructed using kidney-specific megalin partial knockout mice (apoE-Cre), and were used to verify the involvement of megalin in the onset of contrast-induced renal injuries.

Methodology

Left kidneys were extracted from the apoE-Cre knockout mice, and 14 days later, right kidney pedicles were ligated for 30 minutes. Thereafter, reperfusion was carried out. After 24 hours from the start of reperfusion, 200 μL of iomeprol or normal saline was administered from the tail vein.

After 48 hours from the administration, right kidneys were extracted from the animals, and 3 mm-thick sections containing a kidney pedicle portion were prepared from the extracted kidneys, fixed with 4% paraformaldehyde phosphate buffer, sliced at a thickness of 4 μm using a microtome (REM-710; Yamato Kohki Industrial Co., Ltd.), and fluorescently immunostained with anti-megalin and anti-KIM-1 antibodies. The stained slices were mounted with Slow Fade Gold Antifade Reagent (Life Technologies) and observed using a fluorescence microscopy (BZ-9000, Keyence). In particular, it was verified whether megalin and KIM-1 were expressed in the S1 and S2 segments of renal proximal tubules.

Results

Figure 10A:
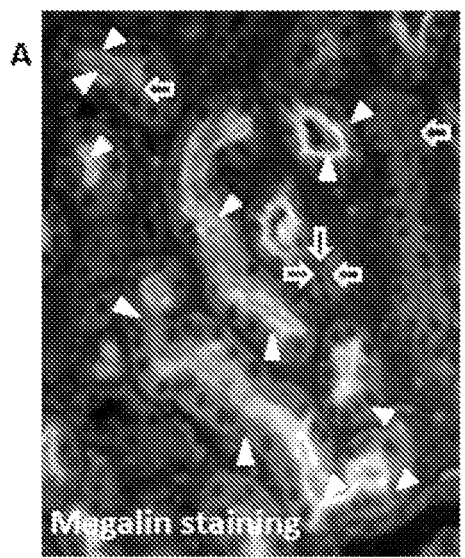
FIG. 10A shows an image of immunohistological staining with an anti-megalin antibody of a kidney sample obtained from a kidney-specific megalin partial knockout mouse (apoE-Cre) after iodinated contrast medium (iomeprol) treatment. Arrow heads (Δ) indicate megalin-expressing portions, and arrows indicate portions with no expression of megalin.
Figure 10B:
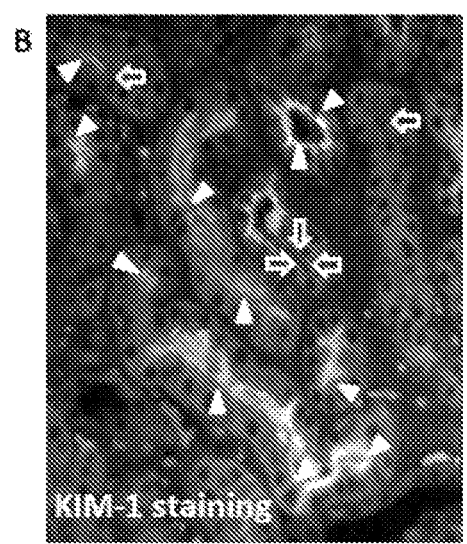
FIG. 10B shows an image of immunohistological staining with an anti-KIM-1 antibody of a kidney sample obtained from a kidney-specific megalin partial knockout mouse (apoE-Cre) after iodinated contrast medium (iomeprol) treatment. Arrow heads (Δ) indicate megalin-expressing portions, and arrows indicate portions with no expression of megalin.
Figure 10C:
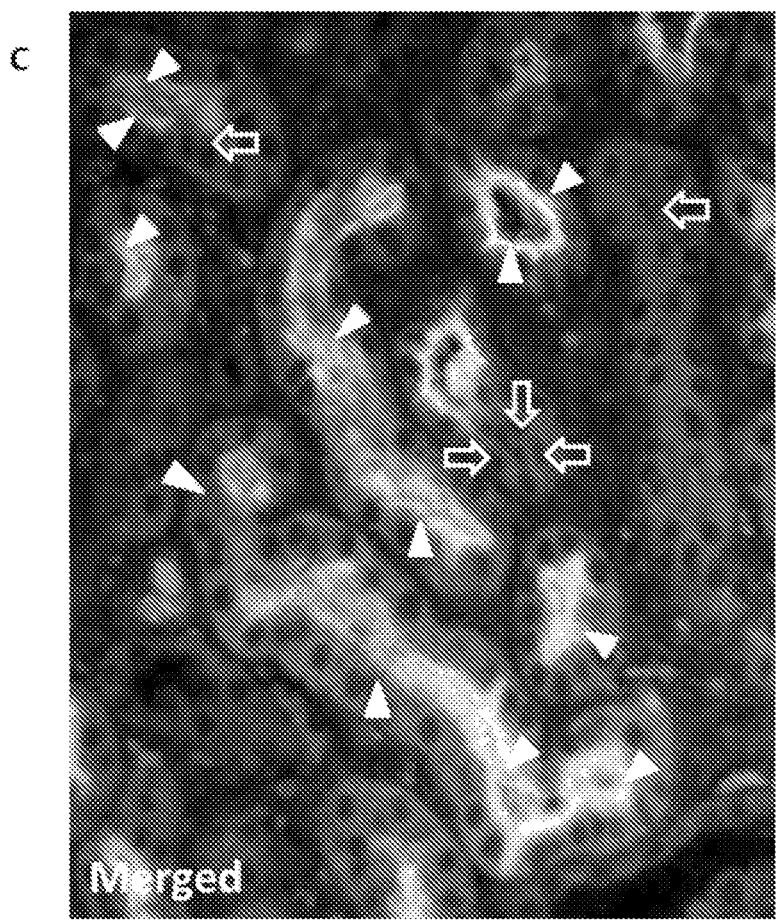
FIG. 10C shows a merged image of the two panels of FIGS. 10A and 10B.

The results are shown in FIGS. 10A to 10C. FIG. 10A shows the result of staining with an anti-megalin antibody (the megalin-expressing regions were stained); FIG. OB shows the result of staining with an anti-KIM-1 antibody (the KIM-1-expressing regions were stained): and FIG. 10C shows a merged image of the two panels of FIGS. 10A and 10B. Renal proximal tubular epithelial cells with expression of megalin are indicated by arrow heads, and those cells with no expression of megalin are indicated by arrows. The regions of megalin expression coincided with those of expression of the injury marker KIM-1. It was found that KIM-1 was expressed in a specific manner in the renal proximal tubular epithelial cells with expression of megalin.

The above results revealed that contrast-induced injury to renal proximal tubular epithelial cells was megalin dependent.

Example 1

In this example, it was verified, using an electron probe microanalyzer (EPMA), whether megalin-dependent internalization of contrast media (iodine) into murine renal proximal tubular epithelial cells was inhibited by treatment with cilastatin.

Methodology

C57BL/6J mice were divided into the following groups and administered with the following agents from the tail vein.

a) Contrast medium+cilastatin-treated groups: 100 μL of iomeprol, iohexol, ioversol or iodixanol+400 mg/kg cilastatin (100 μL)

b) Contrast medium+normal saline-treated groups: 100 μL of iomeprol, iohexol, ioversol or iodixanol+100 μL of normal saline The detailed procedures for preparing and handling samples were performed in accordance with Reference Example 3.

Quantification of Elements in Biological Samples by EPMA

In the "thin-film quantification" technique, simple X-ray intensities vary depending on the fluctuations in the distributions of cellular components and the influence of the thickness of tissue sections, and thus are difficult to compare in a precise and quantitative manner. It is reported that in the measurement of biological samples by EPMA, since nitrogen (N) present in samples constitutes a main component of cell proteins, the distribution of nitrogen corresponds to the distributions of cellular components in a tissue section, and can be used as an internal standard to take into account the fluctuations in the distributions of cellular components and the influence of the thickness of tissue sections (Tanaka, et al., *BMJ Open*, 2014, vol. 4, e004407: and Moriyama, et al., *Am J Respir Crit Care Med*, 2007, vol. 176, p. 70-77).

Therefore, by calculating a ratio of X-ray intensity between iodine (I) and nitrogen (N) (I/N) in a specified area of thin-film biological samples, iodine (I) levels in different samples can be relatively quantified and compared.

$$X\text{-ray count ratio} = (X\text{-ray count of iodine/unit area})/(X\text{-ray count of nitrogen/(unit area)})$$

Based on this principle, iodine levels in a specified area were relatively quantified and compared.

Results

Figure 11:
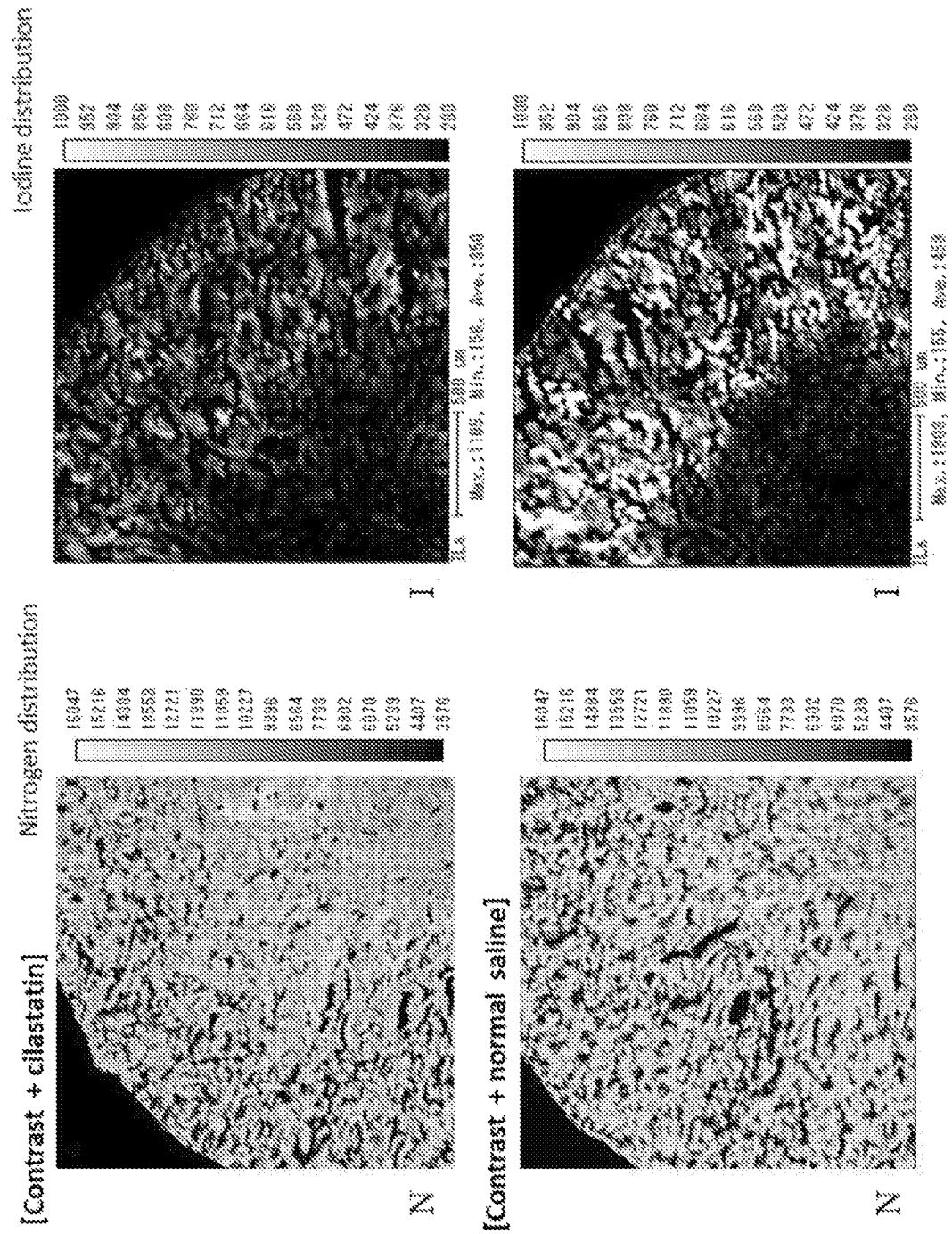
FIG. 11 shows the results of mapping nitrogen (N) and iodine (I) in the kidney tissues obtained from a mouse tested with the treatment with an iodinated contrast medium (iomeprol) and cilastatin, and from a control mouse tested with the treatment with an iodinated contrast medium (iomeprol) and normal saline.
Figure 12:
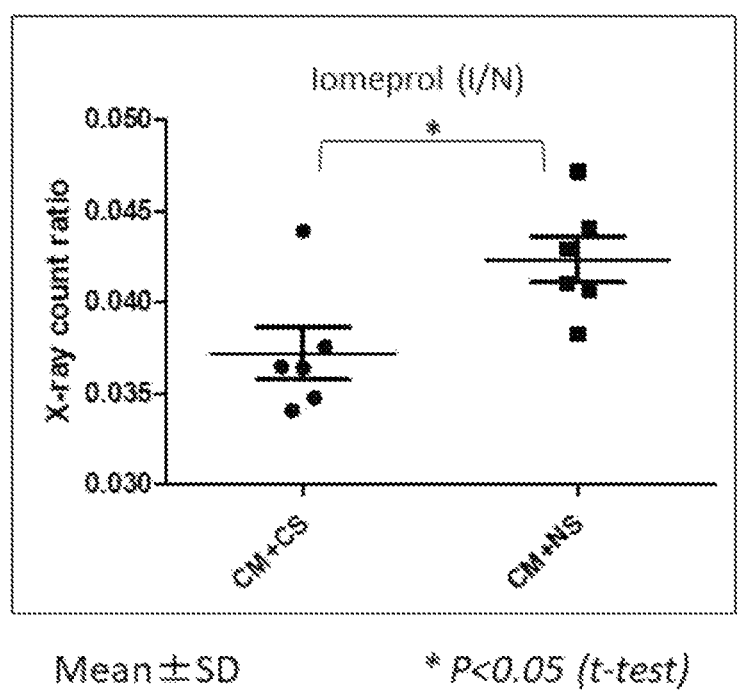
FIG. 12 shows the ratios (I/N ratios) of iodine content to nitrogen content as measured by EPMA in the iodinated contrast medium (iomeprol)+cilastatin-treated mouse group, and the iodinated contrast medium (iomeprol)+normal saline-treated mouse group.
Figure 13:
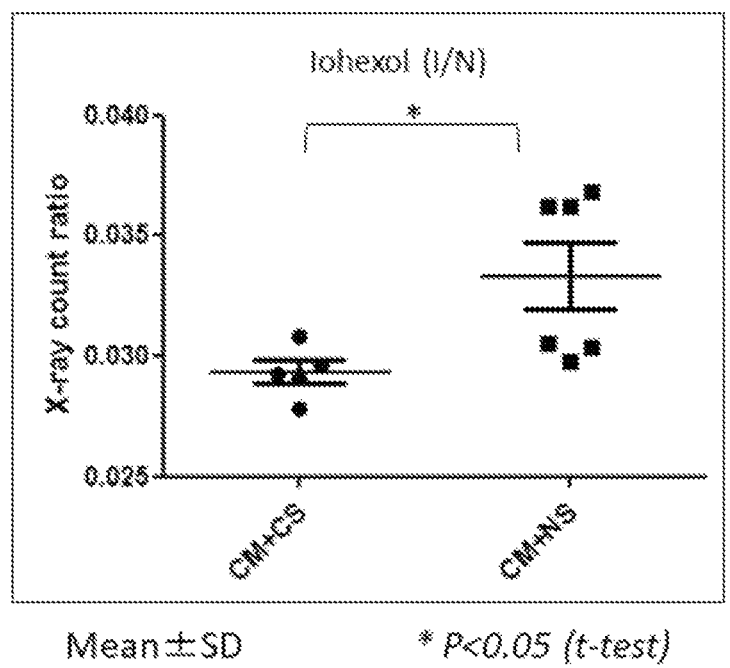
FIG. 13 shows the ratios (I/N ratios) of iodine content to nitrogen content as measured by EPMA in the iodinated contrast medium (iohexol)+cilastatin-treated mouse group, and the iodinated contrast medium (iohexol)+normal saline-treated mouse group.
Figure 14:
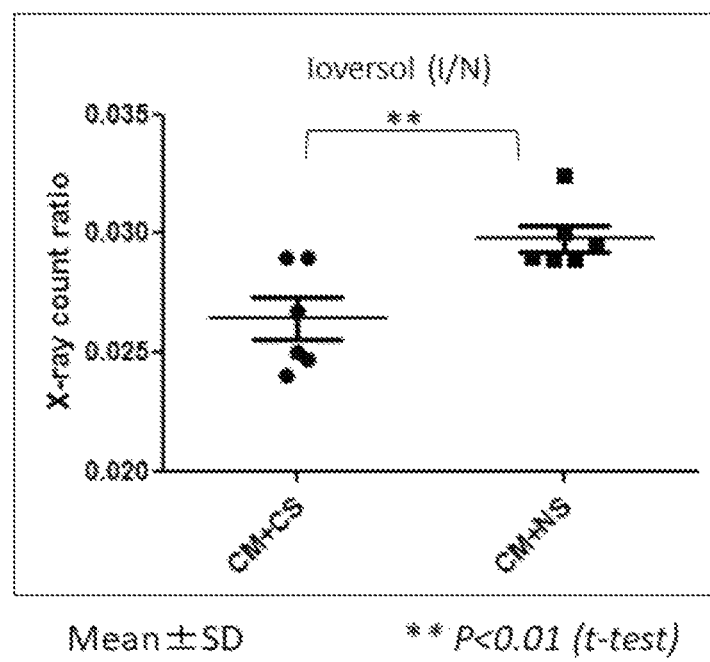
FIG. 14 shows the ratios (I/N ratios) of iodine content to nitrogen content as measured by EPMA in the iodinated contrast medium (ioversol)+cilastatin-treated mouse group, and the iodinated contrast medium (ioversol)+normal saline-treated mouse group.
Figure 15:
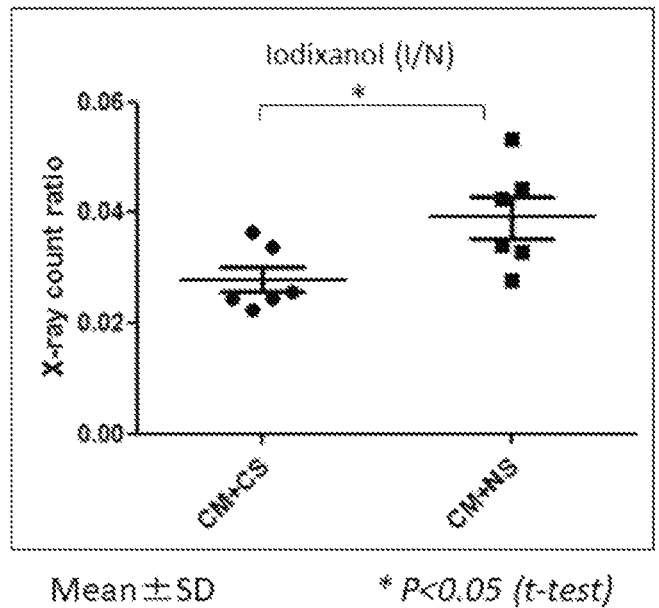
FIG. 15 shows the ratios (I/N ratios) of iodine content to nitrogen content as measured by EPMA in the iodinated contrast medium (iodixanol)+cilastatin-treated mouse group, and the iodinated contrast medium (iodixanol)+normal saline-treated mouse group.

A decrease in the detection of iodine by EMPA was observed in the a) contrast medium+cilastatin-treated groups as compared to the b) contrast medium+normal saline-treated groups (FIG. 11). Further, 1980 μm² regions containing cortex portions were analyzed, and seven 500 μm² areas were chosen from the cortex portions so as not to overlap with each other. An average was calculated of the I/N X-ray ratios in the seven areas, and regarded as an I/N X-ray ratio for one individual. Those I/N X-ray ratios for six individuals in each of the a) and b) groups were quantified and compared. As a result, the 1/N X-ray ratios were significantly (t-test) lower in the a) contrast medium+cilastatin-treated groups than in the b) contrast medium+normal saline-treated groups (FIGS. 12 to 15). In other words, it was found that the levels of iodine found in cortical cells in the analyzed slices were relatively lower in the contrast medium+cilastatin-treated mice.

From the above results, it was considered that cilastatin inhibited internalization of contrast media into renal proximal tubular epithelial cells which constituted much of the cortex portions analyzed. These results, together with the results in Reference Example 2, demonstrated that inhibition of contrast medium internalization by cilastatin is attributed to its antagonizing activity against megalin.

Example 2

In order to confirm the ability of cilastatin to inhibit renal injuries, C57BL/6J mice were simultaneously administered with an iodinated contrast medium and cilastatin, and the results were analyzed.

Methodology

Left kidneys were extracted from the C57BL/6J mice, and 14 days later, right kidney pedicles were ligated for 30 minutes. Thereafter, reperfusion was carried out. After 24 hours from the start of reperfusion, the test animals were divided into the following groups and administered with the following agents from the tail vein.

a) Contrast medium+cilastatin-treated group: 200 μL of iomeprol (CM)+400 mg/kg cilastatin (CS) (100 LL)

b) Contrast medium+normal saline-treated group: 200 μL of iomeprol (CM)+100 μL of NS For each of the groups, after 48 hours from the medication, blood and urine samples were collected, and serum Cr, MN and cystatin C levels, and urinary Cr, NAG and KIM-1 levels were measured. Further, right kidneys were extracted and histologically evaluated by immunostaining with KIM-1 and staining with PAS. The detailed procedures for handling, measurement, and tissue staining to prepare tissues for evaluation were performed in accordance with Reference Example 1. Serum cystatin C and urinary KIM-1 measurements were contracted to Oriental Yeast Co., Ltd.

Immunostaining intensities were scored using the following criteria, based on the method of Zhang, et al. (refer to *Kidney Int,* 2008, vol. 73, p. 608-614).

0: No staining 0.5±: Clear but weak granular staining present focally along the luminal surface of non-atrophic proximal tubules 1+: Clear but weak granular staining completely surrounding the luminal surface of non-atrophic proximal tubules 2+: Moderately intense granular staining completely surrounding the luminal surface of non-atrophic proximal tubules and extending into intercellular junctions 3+: Strong large granular staining completely surrounding the luminal surface of non-atrophic proximal tubules and extending into intercellular junctions Results The criterion of "≥25% increase from baseline serum creatinine" as per the relevant guidelines (NPL 1) was added as a criterion for the onset of contrast nephropathy, and also the criterion of "an individual with KIM-1 expression in the S1 and S2 segments of renal proximal tubules during histological observations" was established to ensure determination of the influence of a contrast medium. Individuals meeting these criteria were regarded as individuals with onset of contrast nephropathy.

The results are shown in FIGS. 16 to 19.

Figure 16:
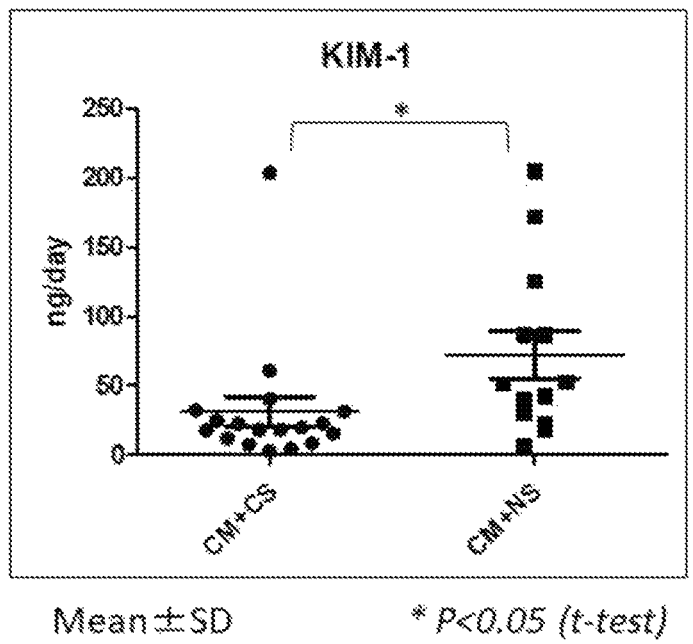
FIG. 16 shows a graph that compares the KIM-1 levels excreted in urine between the iodinated contrast medium (iomeprol)+cilastatin-treated group and the iodinated contrast medium (iomeprol)+normal saline-treated control group.
Figure 17:
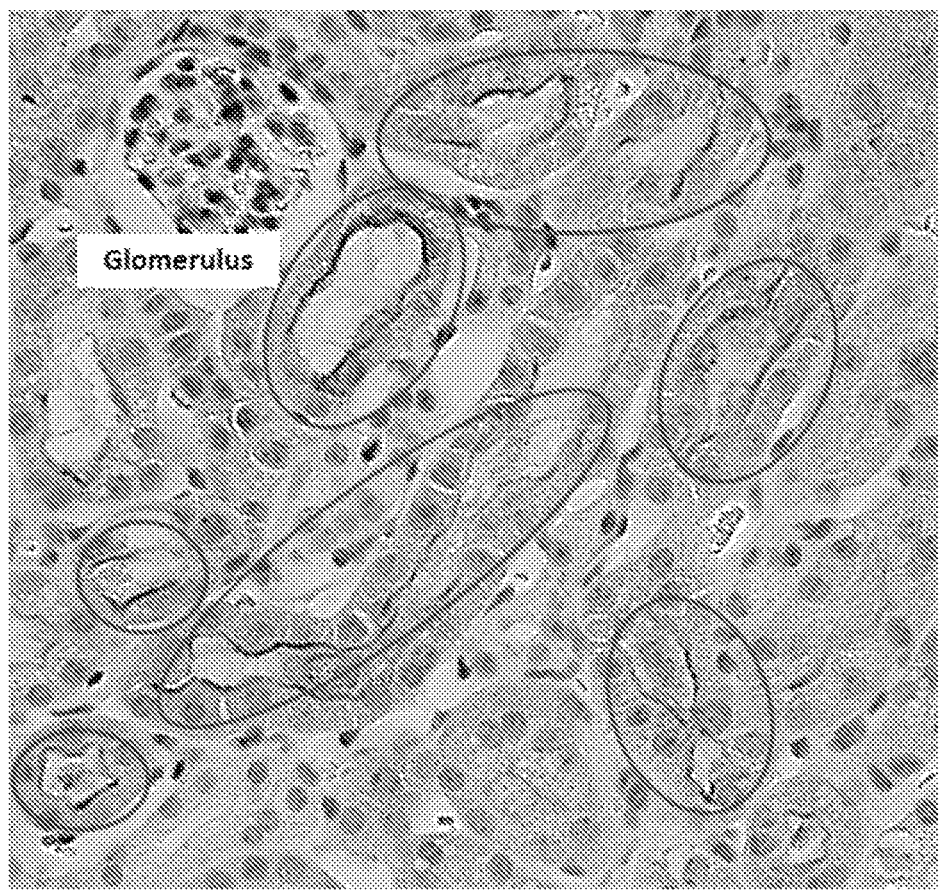
FIG. 17 shows an image of immunostaining with an anti-KIM-1 antibody of a kidney sample from an animal having increased serum creatinine levels after iodinated contrast medium (iomeprol) treatment.

Based on these criteria, the percentages of individuals with onset of contrast nephropathy were 27% in the b) contrast medium+normal saline-treated group, and 0% in the a) contrast medium+cilastatin-treated group. The increase in urinary KIM-1 levels was significantly (t-test) reduced in the a) contrast medium+cilastatin-treated group as compared to the b) contrast medium+normal saline-treated group (FIG. 16).

Figure 18:
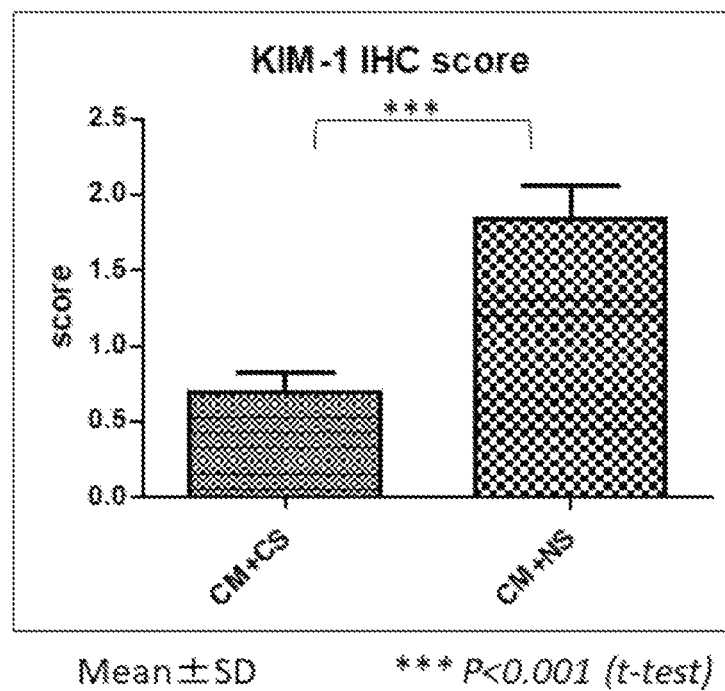
FIG. 18 shows a graph that compares the intensity scores of immunostaining kidney tissues with an anti-KIM-1 antibody between the iodinated contrast medium (iomeprol)+cilastatin-treated group and the iodinated contrast medium (iomeprol)+normal saline-treated control group.
Figure 19:
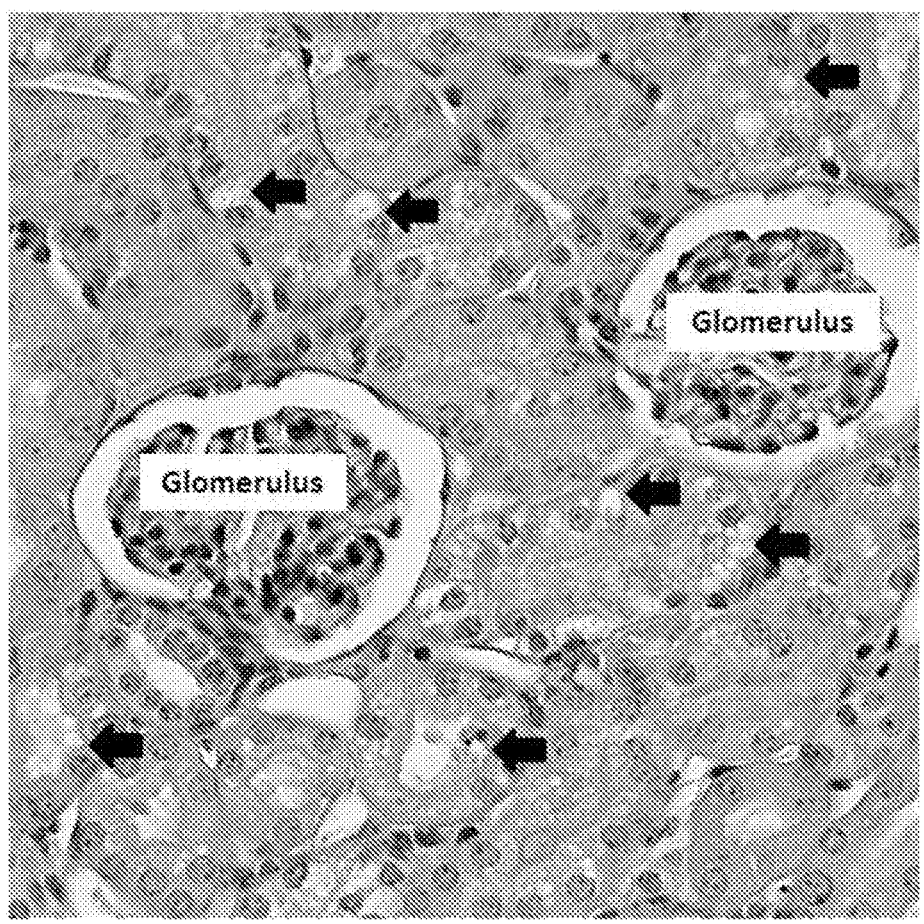
FIG. 19 shows an image of PAS staining of a kidney sample from an animal having increased serum creatinine levels after iodinated contrast medium (iomeprol) treatment.

The expression of KIM-1 in tissues was determined exclusively in the outer cortices containing the S1 and S2 segments in which megalin was highly expressed. In those individuals from the b) contrast medium+normal saline-treated group that had increased serum creatinine levels, KIM-1 was widely expressed, mainly in the S1 and S2 segments (circled portions in FIG. 17). Also, based on the comparison of staining intensity scores, the expression of KIM-1 was significantly (t-test) lower in the contrast medium+cilastatin-treated group (FIG. 18). Further, in the aforementioned individuals from the contrast medium+normal saline-treated group who had increased serum creatinine levels, the formation of vacuoles in renal proximal tubular epithelial cells was observed by PAS staining, likewise mainly in the S1 and S2 segments (as indicated by arrows in FIG. 19).

From the above results, it was found that cilastatin had an ability to inhibit contrast-induced renal injuries. These results, together with the results in reference examples, demonstrated that the ability of cilastatin to inhibit contrast-induced renal injuries is attributed to its antagonizing activity against megalin.

Reference Example 4

Direct binding between an iodinated contrast medium and megalin was verified using contrast solid-phased magnetic beads.

Methodology

1) Preparation of Western Blot (WB) Samples 1-1. Preparation of Iodinated Contrast Medium-Bound Magnetic Beads A starting powder of iodinated contrast medium was dissolved, just before use, in glycidylmethacrylate-coated magnetic beads (FG Beads®, particle size: 0.2 μm, produced by Tamagawa Seiki Co., Ltd.) to initiate chemical bonding between surface carboxyl groups and hydroxyl groups present in the contrast medium, whereby contrast solid-phased magnetic beads were prepared.

The contrast medium iomeprol was purchased from BOC Science.

At feed concentrations of 0 mM, 3 mM and 10 mM, iomeprol was brought to a solid phase by chemical bonding. The preparation of the iomeprol solid-phased beads was contracted to Tamagawa Seiki Co., Ltd.

1-2. Preparation of Brush Border Proteins (BBP)

According to the method of Orlando, et al. (*Proc. Natl. Acad. Sci. USA,* 1992, vol. 89, p. 6698-6702), the cortex portions of Sprague-Dawley (SD) rats were ground to prepare a suspension, which was adjusted to a protein concentration of 1 mg/mL to obtain a BBP solution.

1-3. Preparation of WB Samples

Five milligrams each of the 0 mM and 10 mM contrast solid-phased magnetic beads were dispersed and washed in 200 μL of 100 mM KCL buffer (20 mM HEPES-NaOH (pH 7.9), 100 mM KCl, 1 mM $MgCl_2$, 0.2 mM $CaCl_2$), 0.2 mM EDTA, 10% (v/v) glycerol, 0.1% NP-40, 1 mM DTT, 0.2 mM PMSF).

To each concentration of the washed beads, 200 μL of the BBP solution was added, and the mixture was incubated at 4° C. for 4 hours, magnetically separated to remove the supernatant, and repeatedly dispersed and washed three times in 200 μL of 100 mM KCL buffer. Then, 30 μL of 1 M KCL buffer (prepared by mixing 18 mL of 2.5 M KCl, 7 mL of water, and 25 mL of 2×100 mM KCl buffer, and then by adding 50 μL of 1 M DTT solution and 10 μL of 1 M PMSF solution before use) was added, and the mixture was incubated on ice for 5 minutes. After magnetic separation, the supernatant was added to electrophoresis sample buffer (0.25 M Tris-HCl (pH 6.8), 0.02% BPB, 8% SDS, 40% glycerol, 20% 2-mercaptoethanol), and the mixture was heat treated, whereby each of salt-eluted samples was obtained. Further, electrophoresis sample buffer was added to each of the magnetically separated beads, and the mixture was heated at 98° C. for 5 minutes and magnetically separated to obtain the supernatant. The thus-obtained supernatants were used as heat-eluted samples.

2) Western Blot Analysis Using Anti-Megalin Antibody

The salt-eluted samples and the heat-eluted samples were subjected to SDS electrophoresis under reducing conditions using 4-15% gradient gels (produced by Bio-Rad Laboratories), and the developed samples were transferred onto polyvinylidene fluoride (PVDF) membranes. After blocking with a buffer containing 5% BSA, anti-megalin antibody (C-25 antibody; refer to De, et al., *Diabetes,* 2017, vol. 66, p. 1391-1401) was added at a concentration of 8 μg/mL and reacted at room temperature for 2 hours. HRP-labeled anti-mouse IgG (Dako Ltd.) was added at 1 μg mL and reacted for 1 hour, and then the reactions were examined for the presence of a protein band corresponding to megalin.

Results

Figure 20:
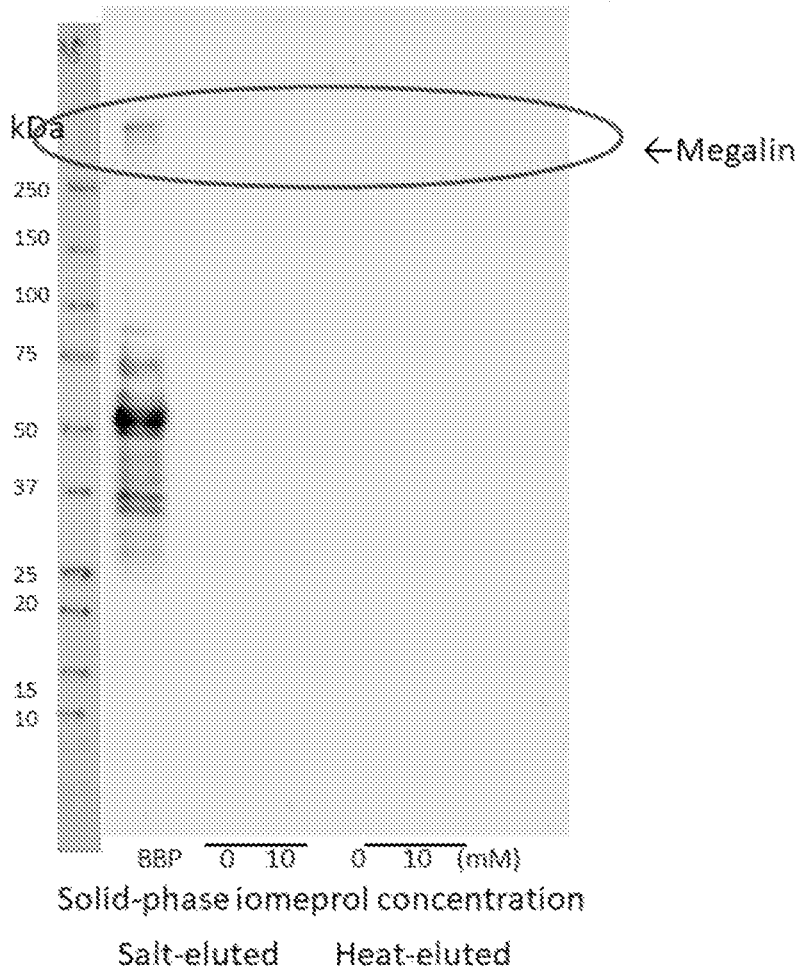
FIG. 20 shows an image of WB analysis (using anti-megalin antibody) of conjugates obtained by reacting iodinated contrast medium (iomeprol)-bound magnetic beads and kidney protein.

As a result of the WB analysis, the megalin band was found in the BBP samples used as a control, but was not detected in the eluted samples obtained after the reaction between BBP and the iodinated contrast medium-bound beads (circled portion in FIG. 20). This revealed that an iodinated contrast medium does not bind directly to megalin.

Considering that it was found in Reference Example 2, etc. that intracellular internalization of iodinated contrast media was megalin dependent, it was suggested that an iodinated contrast medium might bind to megalin not directly but via a carrier substance.

Reference Example 5

A substance that can serve as a carrier for an iodinated contrast medium was selected by reference to the information reported on megalin ligands. To be specific, one protein known to be filtered at the glomeruli and resorbed by renal proximal tubular epithelial cells via megalin was selected among megalin ligands.

The binding specificity between this protein and an iodinated contrast medium was verified using contrast solid-phased magnetic beads by following the procedures described below.

Methodology

1) Preparation of WB Analysis Samples

Five milligrams each of the 0 mM/3 mM/10 mM contrast solid-phased beads prepared in Reference Example 4 were dispersed and washed according to the procedure described in Reference Example 4. Next, the protein of interest (produced by LifeSpan BioSciences, Inc.) was dissolved in 100 mM KCL to prepare a 25 ng/μL solution. The above-washed beads were each dispersed in 200 μL of the prepared solution and reacted at 4° C. for 4 hours. Then, heat-eluted samples were prepared by following the procedure described in Reference Example 4.

2) Western Blot Analysis Using Antibody

The procedures for sample electrophoresis and WB analysis were performed in accordance with Reference Example 4. An antibody against the protein of interest (a polyclonal antibody produced by Bioss Inc.) was added at a concentration of 2 μg/mL and reacted at room temperature for 2 hours.

Results

Figure 21:
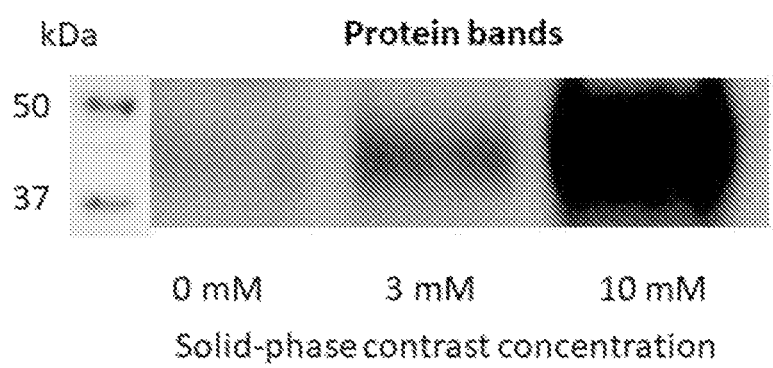
FIG. 21 shows the results of WB analysis of the binding specificity between iodinated contrast medium (iomeprol)-bound magnetic beads and carrier protein.
Figure 22:
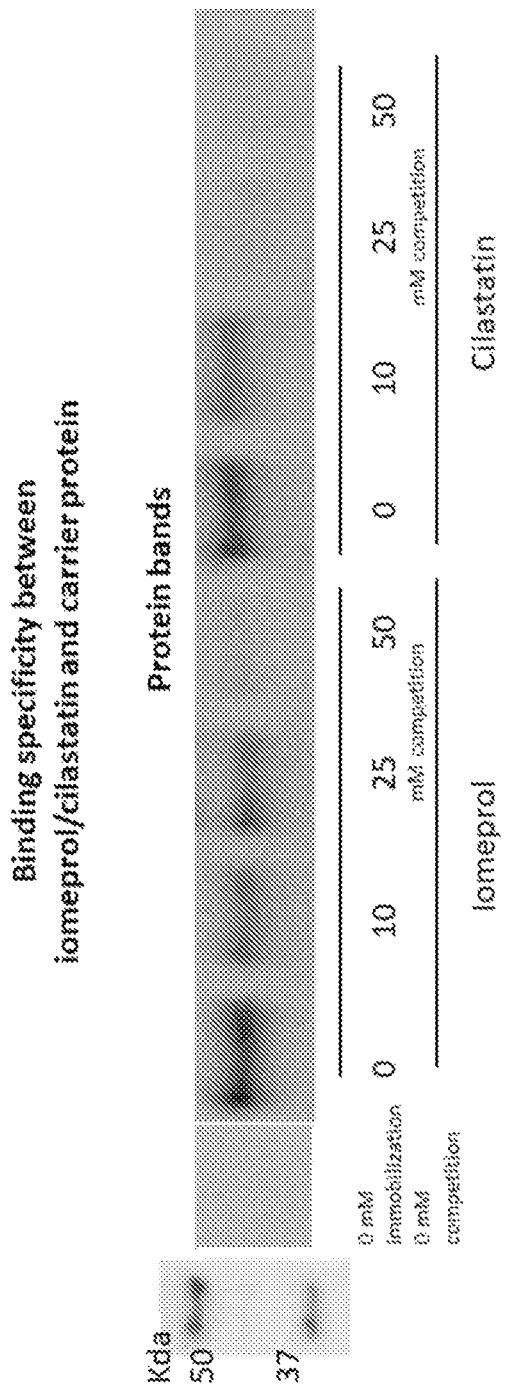
FIG. 22 shows the results of WB analysis of the influence of an iodinated contrast medium (iomeprol) and cilastatin on the reaction between iodinated contrast medium (iomeprol)-bound magnetic beads and carrier protein.
Figure 23:
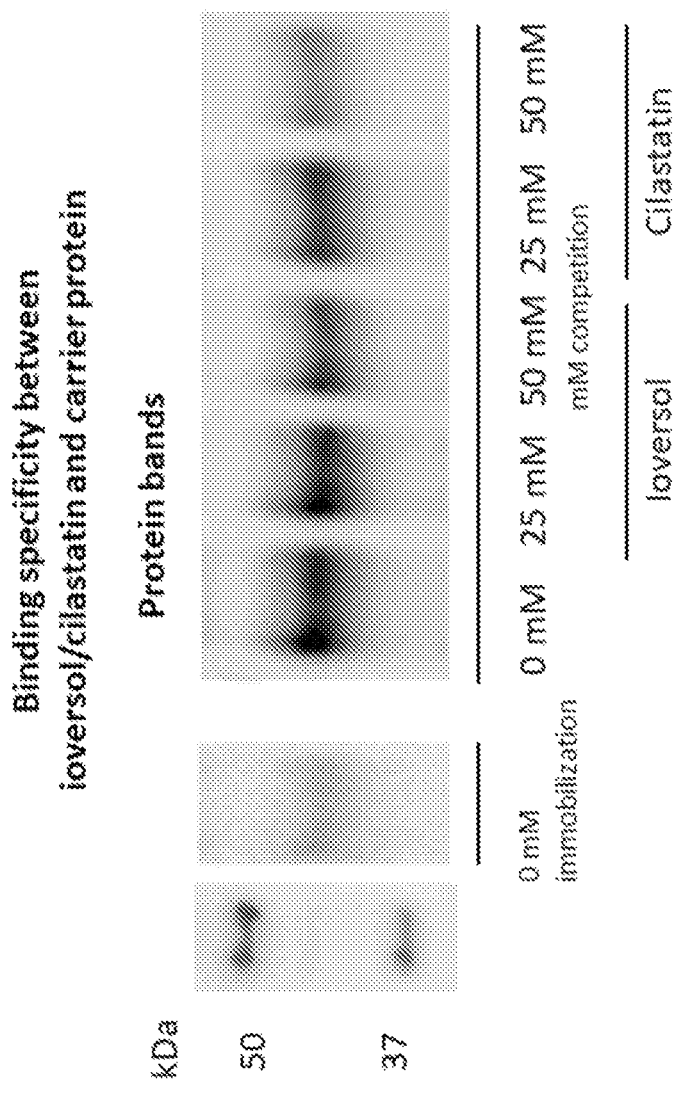
FIG. 23 shows the results of WB analysis of the influence of an iodinated contrast medium (ioversol) and cilastatin on the reaction between iodinated contrast medium (ioversol)-bound magnetic beads and carrier protein.
Figure 24:
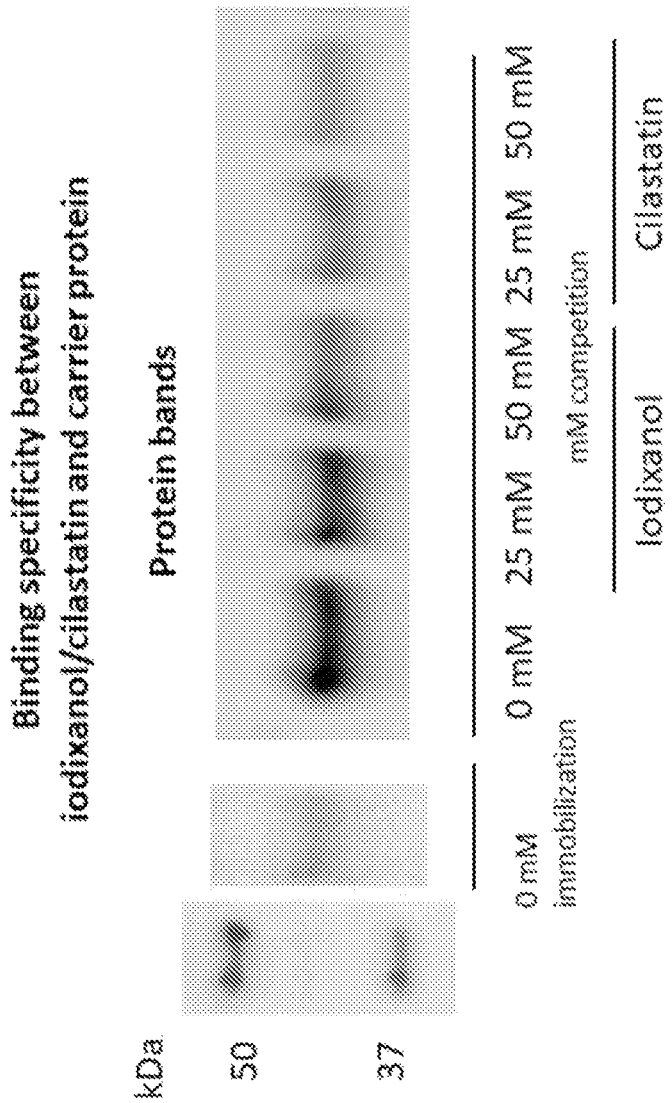
FIG. 24 shows the results of WB analysis of the influence of an iodinated contrast medium (iodixanol) and cilastatin on the reaction between iodinated contrast medium (iodixanol)-bound magnetic beads and carrier protein.
Figure 25:
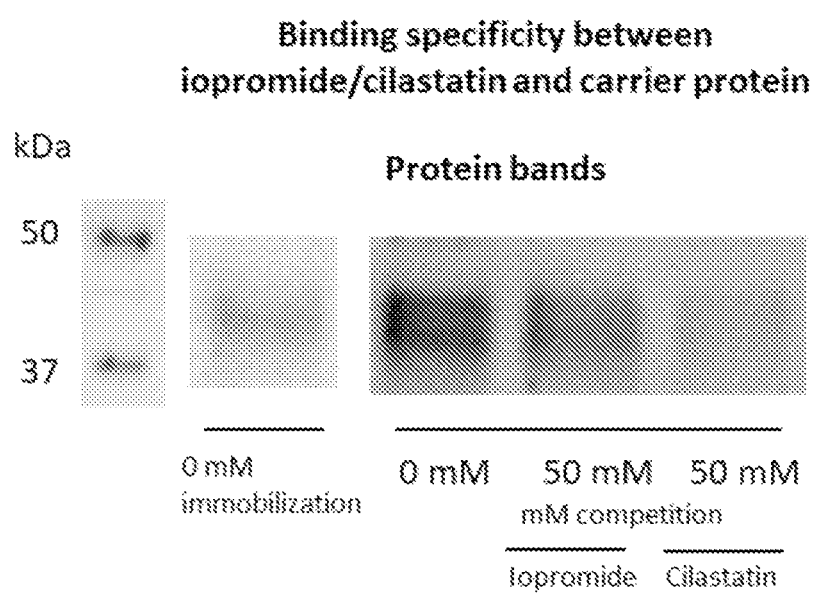
FIG. 25 shows the results of WB analysis of the influence of an iodinated contrast medium (iopromide) and cilastatin on the reaction between iodinated contrast medium (iopromide)-bound magnetic beads and carrier protein.
Figure 26:
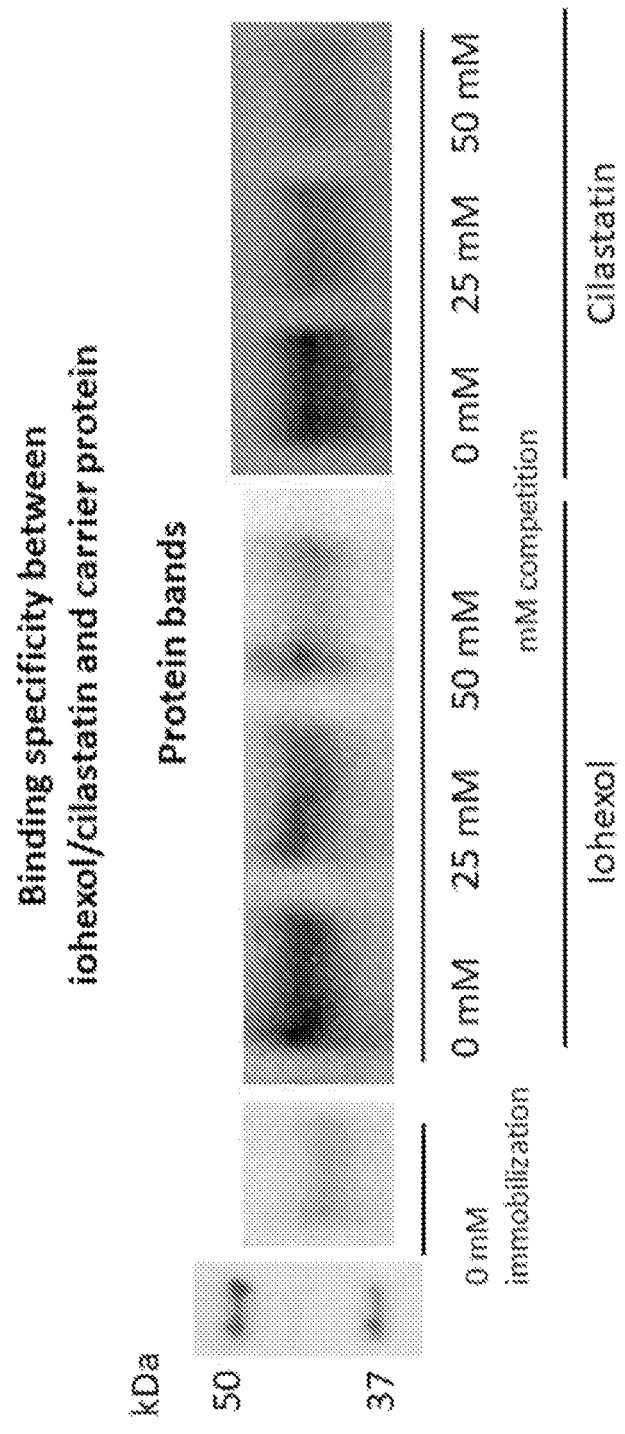
FIG. 26 shows the results of WB analysis of the influence of an iodinated contrast medium (iohexol) and cilastatin on the reaction between iodinated contrast medium (iohexol)-bound magnetic beads and carrier protein.

The results are shown in FIG. 21. It was found that when the concentration of the iodinated contrast medium solid phased on the beads was higher, the intensity of a band corresponding to the molecular weight of the protein of interest from a heat-eluted sample became stronger. Therefore, it was demonstrated that the protein of interest and the contrast solid phased on the beads were bound in a specific manner.

Example 3

From the results in Example 2, it was presumed that the binding between a carrier substance and megalin, and/or the binding between an iodinated contrast medium and a carrier substance might be inhibited by cilastatin.

The binding specificity between iodinated contrast medium (iomeprol, ioversol, iodixanol, iopromide, or iohexol)-bound beads and the protein (carrier) used in Reference Example 5, and the possibility of cilastatin to inhibit this binding were verified.

Methodology

1) Preparation of Samples for Competition Experiments with Contrast Medium

Different solutions, as mentioned below, were prepared using 100 mM KCL buffer (as mentioned in Reference Example 4) and the protein used in Reference Example 5, and were reacted at 4° C. for 2 hours. The contrast medium used was a starting powder of iomeprol (BOC Sciences; 78649-41-9).

a) Solution containing 25 ng/μL of the protein of interest and 0 mM of the contrast medium
b) Solution containing 25 ng/μL of the protein of interest and 10 mM of the contrast medium
c) Solution containing 25 ng/μL of the protein of interest and 25 mM of the contrast medium
d) Solution containing 25 ng/μL of the protein of interest and 50 mM of the contrast medium Next, the above-prepared solutions were each added to 5 mg of the 0 mM or 10 mM contrast solid-phased beads dispersed and washed by the procedure described in Reference Example 4, and were reacted at 4° C. for 4 hours. The solution/beads combinations adopted were as mentioned below.

Solution a)+0 mM contrast solid-phased beads (control)
Solution a)+10 mM contrast solid-phased beads
Solution b)+10 mM contrast solid-phased beads
Solution c)+10 mM contrast solid-phased beads
Solution d)+10 mM contrast solid-phased beads Then, the different mixtures were treated by following the procedure described in Reference Example 4, and heat-eluted samples were prepared from the different reaction solutions.

2) Preparation of Samples for Competition Experiments with Cilastatin

Different solutions, as mentioned below, were prepared using 100 mM KCL buffer (as mentioned in Reference Example 4), and were reacted at 4° C. for 2 hours.

a') Solution containing 25 ng/μL of the protein of interest and 0 mM of cilastatin
b') Solution containing 25 ng/μL of the protein of interest and 10 mM of cilastatin
c') Solution containing 25 ng/μL of the protein of interest and 25 mM of cilastatin
d') Solution containing 25 ng/μL of the protein of interest and 50 mM of cilastatin Next, the above-prepared solutions were each added to 5 mg of the 0 mM or 10 mM contrast solid-phased beads dispersed and washed by the procedure described in Reference Example 4, and were reacted at 4° C. for 4 hours. The solution/beads combinations adopted were as mentioned below.

Solution a')+0 mM contrast solid-phased beads (control)
Solution a')+10 mM contrast solid-phased beads
Solution b')+10 mM contrast solid-phased beads
Solution c')+10 mM contrast solid-phased beads
Solution d')+10 mM contrast solid-phased beads Then, the different mixtures were treated by following the procedure described in Reference Example 4, and heat-eluted samples were prepared from the different reaction solutions.

3) WB Analysis Using Antibody

The different heat-eluted samples obtained in 1) and 2) were subjected to WB analysis by following the procedure described in Reference Example 5.

Further, the same experiments as in 1) to 3) were performed using other contrast media, which were a starting powder of iohexol (Tokyo Chemical Industry Co., Ltd.; 10903), a starting powder of iopromide (Sigma-Aldrich; 1344804-400), a starting powder of iodixanol (The United State Pharmacopeial Convention, Inc.; 1343517), and a starting powder of ioversol (Toronto Research Chemicals Inc.: 1737000). However, experiments regarding some concentrations were omitted.

Results

The results are shown in FIGS. 22-26. Since the band corresponding to the protein of interest was decreased in the coexistence of iodinated contrast media, it was considered that the amount of the protein bound to the contrast-bound beads was reduced by iodinated contrast media. It was found that the protein of interest specifically binds to iodinated contrast media, and that this protein serves as a carrier for iodinated contrast media.

Further, the band corresponding to the protein of interest was decreased also in the coexistence of cilastatin. Thus, it was found that cilastatin was capable of inhibiting the binding between iodinated contrast media and this protein.

Example 4

The binding specificity between megalin and the protein (carrier) used in Reference Example 5, and the possibility of cilastatin to inhibit this binding, were verified by use of quartz crystal microbalance (QCM).

Methodology

According to the method of Orlando, et al, megalin protein purified from Sprague-Dawley (SD) rat kidneys was immobilized on quartz crystals. To be specific, with the use of an immobilization kit for AFFNIX® (Initium Inc.) and according to the recommended protocol for the kit, a megalin protein solution was prepared in Buffer A as provided with the kit to a concentration of 62.5 µg/mL, and placed and immobilized onto quartz crystals mounted in a holder.

After the megalin protein-immobilized quartz crystals were mounted in the measurement instrument AFFINIX® Q8 (Initium Inc.) and the frequency was confirmed to be stable, a recombinant version (1.5 µg) of the protein used in Reference Example 5 was injected (in total injection volume for each injection) to measure frequency overtime. More specifically, the protein of interest was injected in aliquots of the megalin protein-immobilized quartz crystals in 200 µL of buffer to measure frequency. The same measurement was done on quartz crystals, as a control, on which the same amount of bovine serum albumin (BAS) was solid phased instead of megalin. Thus, the specific binding ability of the protein of interest to megalin was analyzed.

Further, aliquots of megalin protein-immobilized quartz crystals in a buffer in which 1 mg of cilastatin was injected in advance were mounted in the measurement instrument, and the frequency was confirmed to be stable, and then, 1.5 µg of the protein of interest was injected to measure frequency over time, whereby the antagonizing activity of cilastatin against the binding of the protein of interest to megalin was analyzed. The same experiment was performed for the control group.

Results

Figure 27:
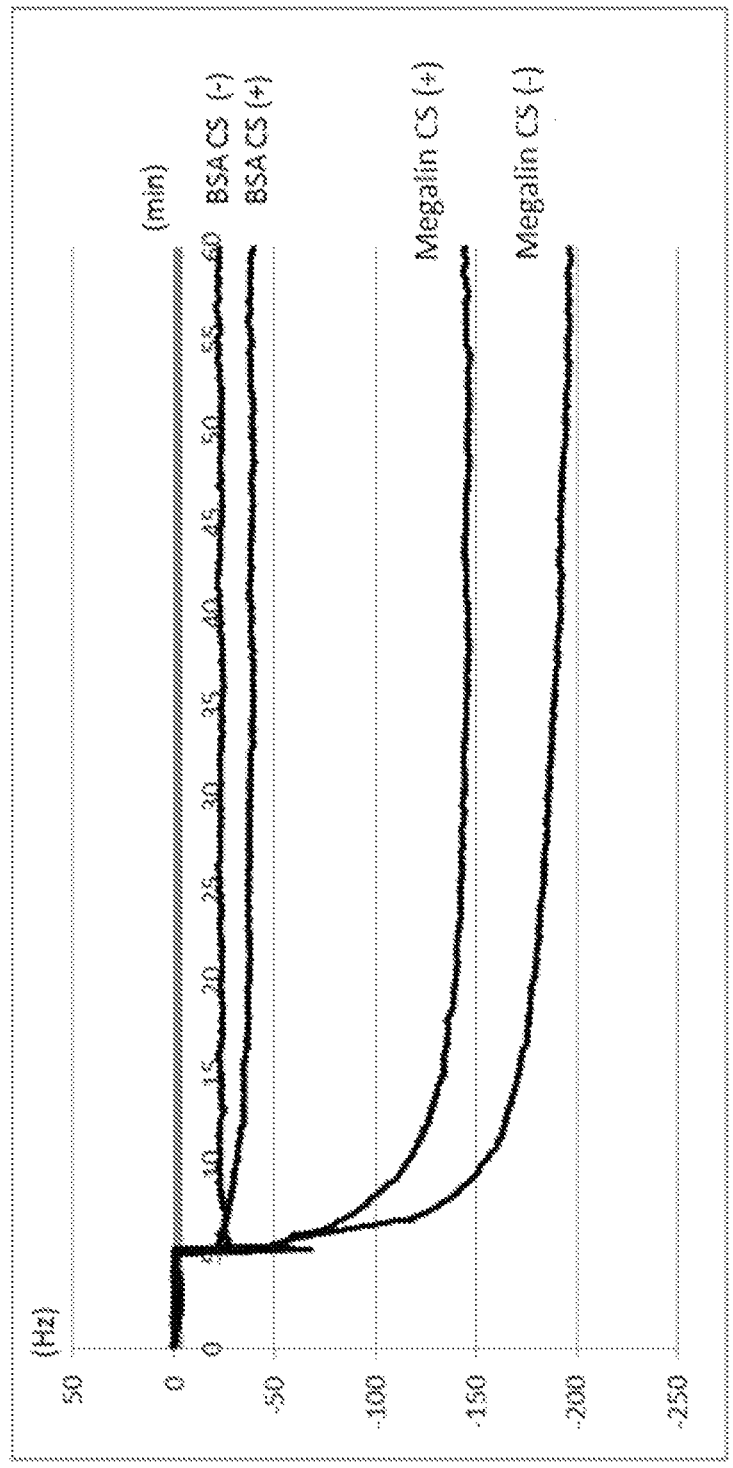
FIG. 27 shows change in frequency over time as measured by the quartz crystal microbalance method, where a carrier protein was added to megalin-immobilized quartz chips (control: BSA-immobilized quartz chips) in the presence or absence of cilastatin.

The results are shown in FIG. 27. The frequencies apparently decreased after the injection of the protein of interest—this demonstrated that the protein of interest bound to megalin.

Also, the change infrequency after the injection of the protein of interest was reduced when cilastatin was injected in advance. This revealed that the binding of the protein of interest to megalin protein was inhibited by cilastatin.

These results, together with the results in Example 3, showed that the binding between the protein of interest and megalin, and the binding between an iodine contrast medium and the protein of interest, are both inhibited by cilastatin. Therefore, it was found that cellular injuries caused by intracellular internalization of iodine contrast media, and renal injuries derived therefrom can be inhibited by cilastatin.

Reference Example 6

Figure 28:
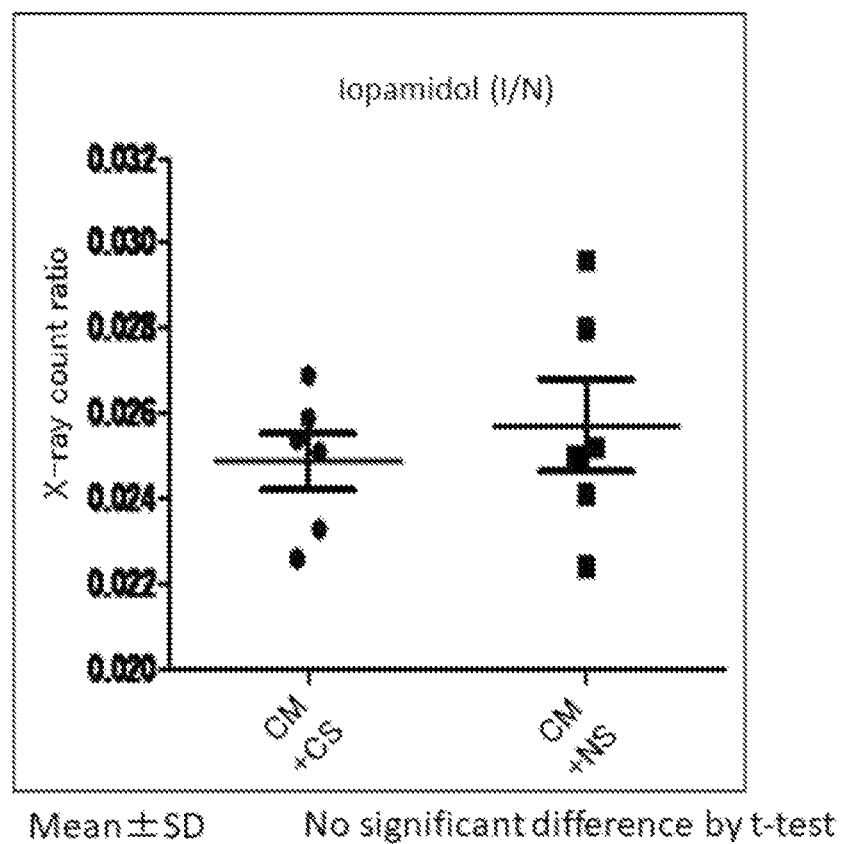
FIG. 28 shows the ratios (I/N ratios) of iodine content to nitrogen content as measured by EPMA in the iodinated contrast medium (iopamidol)+cilastatin-treated mouse group, and the iodinated contrast medium (iopamidol)+normal saline-treated mouse group.
Figure 29:
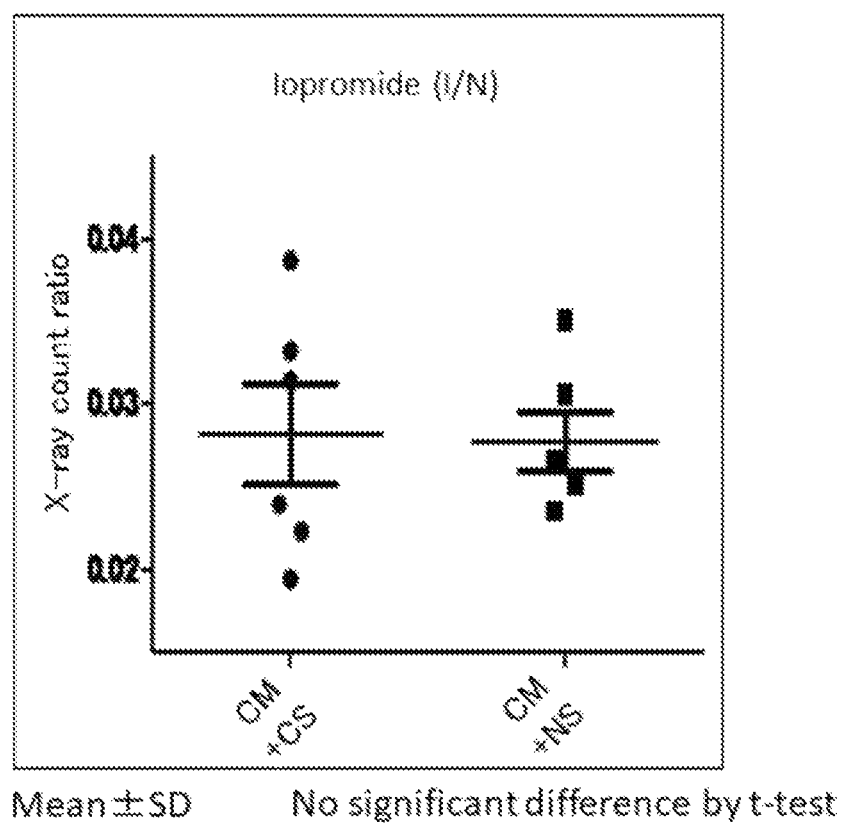
FIG. 29 shows the ratios (I/N ratios) of iodine content to nitrogen content as measured by EPMA in the iodinated contrast medium (iopromide)+cilastatin-treated mouse group, and the iodinated contrast medium (iopromide)+normal saline-treated mouse group.

The same experiment as in Example 1 was conducted using each of iopamidol and iopromide. The EPMA measurement results thus obtained are shown in FIGS. 28 and 29.

INDUSTRIAL APPLICABILITY

The present invention can provide an inhibitor for renal injuries induced by an iodinated contrast medium.

The invention claimed is:

1. A method for inhibiting renal injuries induced by an iodinated contrast medium, the method comprising administering to a subject in need thereof an inhibitor comprising cilastatin or a pharmaceutically acceptable salt thereof as an active component, wherein the iodinated contrast medium is selected from the group consisting of ioversol, iomeprol, iodixanol, and pharmaceutically acceptable salts thereof.

2. The method for inhibiting renal injuries according to claim 1, wherein the iodinated contrast medium is selected from the group consisting of iomeprol, iodixanol, and pharmaceutically acceptable salts thereof.

3. The method for inhibiting renal injuries according to claim 1, wherein the inhibitor is in an injectable form.

4. The method for inhibiting renal injuries according to claim 2, wherein the inhibitor is in an injectable form.

5. The method for inhibiting renal injuries according to claim 1, wherein the iodinated contrast medium is ioversol or a pharmaceutically acceptable salt thereof.

6. The method for inhibiting renal injuries according to claim 1, wherein the iodinated contrast medium is iomeprol or a pharmaceutically acceptable salt thereof.

7. The method for inhibiting renal injuries according to claim 1, wherein the iodinated contrast medium is iodixanol or a pharmaceutically acceptable salt thereof.

* * * * *